United States Patent
Mimoto et al.

(10) Patent No.: US 6,673,772 B2
(45) Date of Patent: Jan. 6, 2004

(54) DIPEPTIDE COMPOUNDS AND THEIR USE AS ANTIVIRAL AGENTS

(75) Inventors: Tsutomu Mimoto, Toda (JP); Keisuke Terashima, Toda (JP); Haruso Takaku, Toda (JP); Shinji Matsumoto, Toda (JP); Makoto Shintani, Toda (JP); Satoshi Nojima, Toda (JP)

(73) Assignee: Sumitomo Pharmaceuticals Company Limited, Osaka (JP)

( * ) Notice: Subject to any disclaimer, the term of this patent is extended or adjusted under 35 U.S.C. 154(b) by 185 days.

(21) Appl. No.: 09/939,858

(22) Filed: Aug. 27, 2001

(65) Prior Publication Data

US 2002/0049165 A1 Apr. 25, 2002

Related U.S. Application Data

(63) Continuation of application No. PCT/JP00/09361, filed on Dec. 28, 2000.

(51) Int. Cl.[7] .................................. C07K 5/06
(52) U.S. Cl. ......................... 514/19; 548/535
(58) Field of Search ............................. 514/19; 548/535

(56) References Cited

U.S. PATENT DOCUMENTS 6,313,094 B1 * 11/2001 Mimoto ................... 514/18

OTHER PUBLICATIONS

Mimoto, J. Med. Chem 42, 1789, 1999.*
Enomoto, et al., "Structure–activity relationships of tripeptide HIV protease inhibitors containing the hydroxymethylcarbonyl isostere", *Peptide Chemistry*, 1993 31st, pp 181–4.
Takashiro, E., et al., "Structure–Activity Relationship of HIV–1 Protease Inhibitors Containing α–Hydroxy–β–amino Acids. Detailed Study of $P_1$ Site", *Bioorg. Med. Chem.*, 1999, 7(9), p. 2063–2072.
Abdel–Rahman, et al., *Allophenylnorstatine Containing HIV–1 Protease Inhibitors: Design, Synthesis and Structure–Activity Relationships for Selected P2 Ligands*, (1997), First International Peptide Symposium Program & Abstracts, p–206.
Yoshimura, et al., *A dipeptide protease inhibitor (PI) that potently inhibits multi–PI–resistant HIV–1*, (1999), Proc. Natl. Acad. Sci. USA, vol. 96, pp. 8675–8680.
Humphrey, et al., *A phase I trial of the pharmacokinetics, toxicity, and activity of KNI–272, an inhibitor of HIV–1 protease, in patients with AIDS or symptomatic HIV infection*, (1999) Antiviral Research 41, 21–33.
Sato, et al., *Invitro antiviral activity and pharmacokinetic (PK) profiles of KNI 272 when combined with other protease inhibitors (PIs)*, (1998), 12th World AIDS Conference, Geneva.

Ueno, et al., *Anti–HIV–1 activity of and HIV–1 resistance profiles against JE–2147 (KNI–764) a novel inhibitor of HIV–1 protease*, (1998), 12th World AIDS Conference, Geneva.
Kato, et al., *Importance of Molecular Flexibility for the Resistance of HIV–1 Protease Inhibitors*, (1998), 12th World AIDS Conference, Geneva.
Ueno, et al., *Pharmacokinetics and oral bioavailability of a novel HIV protease inhibitor JE–2147 (KNI–764) in animals*, (1998), 12th World AIDS Conference, Geneva.
Nakashima, et al., *A Novel–Anti–human Immunodeficiency Virus (HIV) Peptide Produced by Streptomyces, Shows Synergistic Antiviral Activities with HIV Protease Inhibitor and 2',3'—Dideoxynucleosides*, (1996), Biol. Pharm. Bull. 19(3) 405–412.
Mimoto, et al., *A novel dipeptide–based HIV protease inhibitor containing allophenylnorstatine*, (1999), Peptide Science—Present and Future, 652–53.
Bekhit, et al., *Allophenylnorstatine containing HIV–1 protease inhibitors: design, synthesis and structure–activity relationships for selected P2 and P2' ligands*, (1999), Peptide Science—Present and Future, 660–61.

(List continued on next page.)

Primary Examiner—Christopher S. F. Low
Assistant Examiner—David Lukton
(74) *Attorney, Agent, or Firm*—Palmer and Dodge, LLP

(57) ABSTRACT

A novel dipeptide compound inhibiting the enzymatic activity of HIV protease and an anti-AIDS medicine comprising this dipeptide compound as an effective component represented by formula (I)

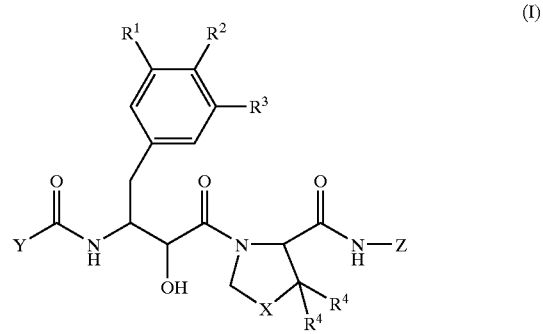

(I)

wherein $R^1$, $R^2$, and $R^3$ independently represent $C_{1-4}$ alkyl, alkoxyl, hydrogen etc ... (provided that not all of the $R^1$, $R^2$, and $R^3$ are hydrogen), $R^2$ and $R^3$ may form a ring together, $R^4$ represents $C_{1-4}$ alkyl or hydrogen; X is a methylene group or a sulfur atom; Y represents e.g., a five or six member monocycle or aryloxyalkyl having up to 12 carbon atoms (provided that the aromatic ring may be substituted by alkyl etc ... ); and Z represents a $C_{1-6}$ aliphatic hydrocarbon or an aromatic hydrocarbon having up to 12 carbon atoms (provided that this aromatic ring may be substituted by alkyl etc . . . , or at least one carbon atom in the aromatic hydrocarbon may be replaced by a hereto atom).

15 Claims, 1 Drawing Sheet

OTHER PUBLICATIONS

Abdel–Rahman, et al., *Allophenylnorstatine containing HIV–1 protease inhibitors: design, synthesis and structure–activity relationships for selected P2 ligands*, (1999), Peptide Science—Present and Future, 662–63.

Shimohigashi, et al., *Structural Essentials for Novel Inhibition of Serine Proteinase Chymotrypsin*, (1997), First International Peptide Symposium Program & Abstracts, p–201.

Mimoto, et al., *A Novel Dipeptide–Based HIV Protease Inhibitor Containing Allophenylnorstatine*, (1997), First International Peptide Symposium Program & Abstracts, p–202.

Bekhit, et al., *Allophenylnorstatine Containing HIV–1 Protease Inhibitors: Sesign, Synthesis and Structure–activity Relationships for Selected P2 an P2' ligands*, (1997), First International Peptide Symposium Program & Abstracts, p–205.

Mimoto, et al., *Structure–Activity Relationship of Small–Sized HIV Protease Inhibitors Containing Allophenylnorstatine*, (1999), J. Med. Chem. 42, 1789–1802.

Mimoto, et al., *Structure–Activity Relationship of Orally Potent Tripeptide–Based HIV Protease Inhibitors Containing Hydroxymethylcarbonyl Isostere*, (2000), Chem. Pharm. Bull. 48(9) 1310–1326.

Humphrey, et al., *Removal of Human Immunodeficiency Virus Type 1 (HIV–1) Protease Inhibitors from Preparations of Immature HIV–1 Virions Does Not Result in an Increase in Infectivity or the Appearance of Mature Morphology*, (1997), Antimicrobial Agents and Chemotherapy, vol. 41, No. 5, p. 1017–1023.

Thaistivongs, et al., *A Novel Nonpeptidic Inhibitor of the HIV Protease*, (1997), Sixth European Conference on Clinical Aspets and Treatment of HIV–Infection Hamburg, Germany Abstract Book, section 331–339.

Kiso, et al., *Small–sized HIV protease inhibitors containing the hyroxymethylcarbonyl isostere as an ideal transition–state mimic*, (1997), International Conference on Protease Inhibitors '97 Program and Abstracts, p. 22.

Mimoto, et al., *A Novel Dipeptide–based HIV Protease Inhibitor Containing Allophenylnorstatine*, (1997), International Conference on Protease Inhibitors '97 Program and Abstracts, p. 52.

Luo, et al., *Dynamic Flexibility of Protein–Inhibitor Complexes: A Study of the HIV_1 Protease/KNI–272 Complex*, (1998), J. Am. Chem. Soc., 120, 12410–12418.

Sato, et al., *Efficacy of KNI–272 in Combination with Other Antiviral Agent*; (1997); Aids Research Newsletter pp. 46–48.

Mitoguchi, et al., *Small–sized HIV Protease Inhibitors Containing Allophenylnorstatine as a Substrate Transition–state Mimic*, (1995), Peptide Chemistry, Protein Research Foundation pp. 373–376.

Yamaguchi, et al., *Synthesis of HIV Protease Dipeptide Inhibitors and Prodrugs*, (1996), Peptide Chemistry, Protein Research Foundation pp. 297–300.

Kiso, et al., *Potent dipeptide HIV protease inhibitors containing the hydroxymethylcarbonyl isostere as an ideal transition–state mimetic*, (1999), Peptides: Frontiers of peptide science, pp. 667–669.

Kiso, et al., *Small Peptidomimetic HIV Protease Inhibitors Containing Allophenylnorstatine Exhibit Antiviral Activities*, (1996), Peptides 1996, pp. 541–542.

Erickson, et al., *The not–so–great escape drug resistance studies with HIV protease*, National Library of Medicine, MEDI, Section 261.

Kiso, et al., *KNI–577, a Potent Small–Sized HIV Protease Inhibitor Based on the Dipeptide Containing the Hydroxymethylcarbonyl Isostere as an Ideal Transition–State Mimic*, (1998), Arch. Pharm. Pharm. Med. Chem., pp. 87–89.

Patick, et al., *Antiviral Activity and Resistance Profile of AG1776, A Novel Inhibitor of HIV–1 Protease*, (1999), 6th Conference on Retroviruses and Opportunistic Infections.

Doi, et al., *KNI–272, a highly selective and potent peptidic HIV protease inhibitor*, (2001_), Acta Cryst. C57, 1333–1335.

Sheha, et al., *Synthesis of di– and tripeptide analogues containing α–ketoamide as a new core structure for inhibition of HIV–1 protease*, (2000), Eur. J. Med. Chem. 35, 887–894.

Hideya, et al., *Evaluation and preclinical test of proposed new HIV protease inhibitor remedy using SIV infected monkey model*, (1998), Kokusai Kenkyu Guranto Jiggyo Kenkyu Hokokusho, p. 112–121, fig. 3, tbl. 3, ref. 21.

Hideya, et al., *Structual analysis of a drug resistant HIV protease and development of a new HIV protease inhibitor*, (1997), Kokusai Kenkyu Guranto Jiggyo Kenkyu Hokokusho, p. 13–25, fig. 4, tbl. 5, ref. 16.

* cited by examiner

SEQUENCE LISTING

<160> NUMBER OF SEQ ID NOS: 1

<210> SEQ ID NO 1
<211> LENGTH: 7
<212> TYPE: PRT
<213> ORGANISM: Human immunodeficiency virus type 1

<400> SEQUENCE: 1

Ser Gln Asn Tyr Pro Ile Val
1               5

DIPEPTIDE COMPOUNDS AND THEIR USE AS ANTIVIRAL AGENTS

This application is a continuation of PCT/JP00/09361, filed Dec. 28, 2000.

TECHNICAL FIELD

The present invention relates to a novel dipeptide compound which inhibits enzymatic activity of an HIV protease and to an anti-AIDS medicine which suppresses in vivo HIV growth utilizing the HIV protease inhibitory activity of the dipeptide compound.

DESCRIPTION OF BACKGROUND ART

Human immunodeficiency viruses (HIV) which induce AIDS produce a Gag protein, reverse transcriptase, or the like used for formation of the viruses as a precursor protein in host cells. The precursor proteins can function only when cut into a specific size using a protease (HIV protease) originating from viruses. An HIV protease inhibitor which inhibits the activity of the HIV protease and thereby blocks formation and maturation of infectious virus particles can be used as an anti-virus agent. Several such HIV protease inhibitors have already been reported.

One kind of such compounds is synthetic peptide-like compounds called a substrate transition state mimetic (T. Robins et al., J. Acquire. Immun. Defic. Syndr., 6, 162, 1993, etc.). The compounds which have been reported to be useful as an HIV protease inhibitor include a hydroxyethyl amine derivative such as Ro31-8959 which contains a phenylalanine φ [CH(OH)CH$_2$N] decahydroisoquinoline carboxylic acid skeleton similar to an amino acid sequence selectively cut by an HIV protease, -Tyr*Pro-, or -Phe*Pro-(N. A. Roberts, et al., Science, 248, 358–361, 1990), a hydroxymethylcarboxamide derivative such as a peptide containing a phenylalanine φ [CH(OH)CON] proline-like skeleton (T. F. Tam, et al., J. Med. Chem., 35, 1318–1320, 1992), and the like.

The inventors of the present invention have previously found that a synthetic peptide compound containing a 3-amino-2-hydroxy-4-phenylbutanoic acid in the skeleton structure strongly inhibits HIV protease activity and is useful as an anti-AIDS medicine. The inventors have proposed such a peptide as an HIV protease inhibitor (Japanese Patent Application Laid-open No. 10-025242, etc.).

However, when administering such an HIV protease inhibitor orally or parenterally, it is difficult to maintain its concentration in blood sufficiently high to suppress duplication of viruses in infected cells in the body. Quite a few HIV protease inhibitors therefore remain still in the clinical test stage. One reason for this is incapability of the medical component to reach inside the cells due to interaction with proteins (particularly α$_1$-acidic glycoproteins) which are present in plasma (e.g. J. K. Lazdins, et al., The Journal of Infectious Diseases, 175, 1063–1070, 1997). In view of this situation, development of a compound exhibiting a strong anti-virus action which is less affected by plasma proteins has been desired.

DISCLOSURE OF THE INVENTION

The present invention has been achieved in view of the above situation and has an object of providing a novel dipeptide compound which can exhibit a strong action and can maintain a high concentration in cells in the presence of plasma proteins, as compared with conventional HIV protease inhibitors comprising a substrate transition state mimetic peptide compound heretofore proposed as an anti-AIDS medicine. Another object of the present invention is to provide an anti-AIDS medicine comprising the novel dipeptide compound as an effective component, which can achieve a curative effect at a small dose.

The present invention relates to novel dipeptide compounds represented by the following formula (I) or (II), or pharmaceutically acceptable salts thereof,

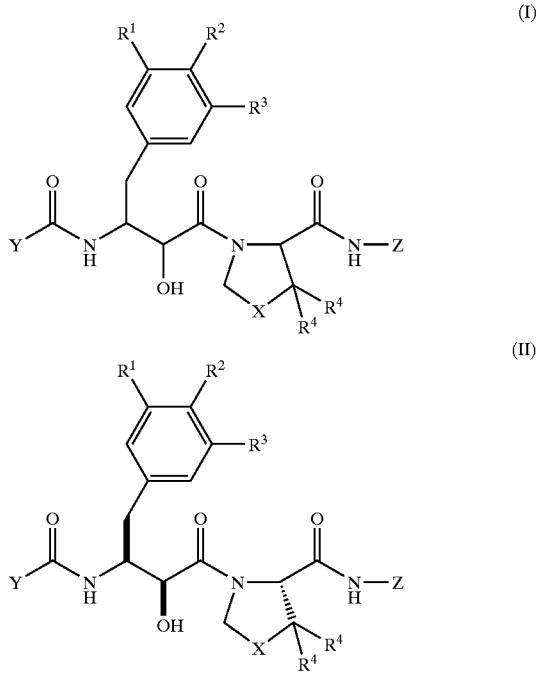

wherein $R^1$, $R^2$, and $R^3$ independently represent a linear or branched, saturated or unsaturated lower alkyl group, alkoxyl group, alkylamino group, or dialkylamino group having 1–4 carbon atoms (with a carbon atom being either replaced by an oxygen atom or not), a halogeno group, or a hydrogen atom, provided that all of the $R^1$, $R^2$, and $R^3$ are not a hydrogen atom at the same, $R^2$ and $R^3$ may form a ring together; $R^4$ represents a linear or branched lower alkyl group having 1–4 carbon atoms or a hydrogen atom; X is a methylene group or a sulfur atom; Y represents a five or six member monocyclic or polycyclic hydrocarbon group, a heterocyclic group having a structure in which one or more carbon atom in the monocyclic or polycyclic hydrocarbon group is replaced by a hetero atom, an aryloxyalkyl group having 12 or less carbon atoms, in which the aromatic ring may be substituted with an alkyl group, alkoxy group, halogeno group, amino group or hydroxyl group; and Z represents an aliphatic hydrocarbon group having 1–6 carbon atoms or an aromatic hydrocarbon group having 12 or less carbon atoms in which the aromatic ring may be substituted with an alkyl group, alkoxy group, or halogeno group, or one or more carbon atom in the aromatic hydrocarbon group may be replaced by a hetero atom.

The present invention preferably relates to a dipeptide compound of the above formula (I) or (II), in which Y is a group represented by the following formula (III) or (IV), and Z is a group represented by the following formula (V) or a linear or branched lower alkyl group having 6 or less carbon atoms, or a pharmaceutically acceptable salt thereof,

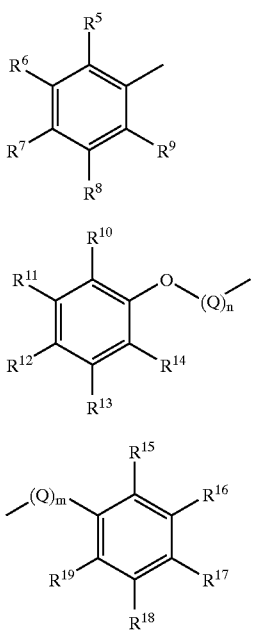

(III)

(IV)

(V)

wherein $R^5$ represents a linear or branched lower alkyl group having 1–4 carbon atoms or a halogeno group, $R^6$ represents an amino group or hydroxyl group, $R^7$, $R^8$, and $R^9$ represent a hydrogen, a methyl group, or a fluoro group, $R^{10}$–$R^{14}$ individually represent a linear or branched lower alkyl or alkoxy group having 1–4 carbon atoms, a halogeno group, or a hydroxyl group,
$R^{15}$–$R^{19}$ individually represent a linear or branched lower alkyl or alkoxy group having 1–4 carbon atoms, a halogeno group, or a hydrogen atom, Q is an alkylene group, n is 0 or 1, and m is 0–6.

The present invention preferably relates to a novel dipeptide compound having a methyl group for $R^4$ and a sulfur atom for X in the above formula (I) or (II), and to a pharmaceutically acceptable salt thereof.

The other preferable compounds of the present invention is a novel dipeptide compound having the group of the formula (III) for Y and the group of the formula (V) for Z in the above formula (I) or (II), and a pharmaceutically acceptable salt thereof. In this instance, preferably $R^5$ is a methyl group or a chloro group, $R^6$ is a hydroxyl group or amino group, and $R^7$–$R^9$ are a hydrogen, and more preferably $R^{15}$ is a methyl group, $R^{16}$–$R^{18}$ is a hydrogen, and $R^{19}$ is a methyl group or a hydrogen.

Furthermore, among the dipeptide compounds or pharmaceutically acceptable salts thereof, having the group of the formula (III) for Y, the group of the formula (V) for Z, a methyl group or chloro group for $R^5$, a hydroxyl group or amino group for $R^6$, a hydrogen for $R^7$–$R^9$, a methyl group for $R^{15}$, a hydrogen for $R^{16}$–$R^{18}$, and a methyl group or hydrogen for $R^{19}$ in the above formula (I) or (II), a compound having a hydrogen for $R^1$, a linear or branched, saturated or unsaturated lower alkoxy group having 1–4 carbon atoms, in which the carbon atoms may be replaced by oxygen atoms, or a hydrogen for $R^2$ or $R^3$ ($R^2$ and $R^3$ must not be hydrogen at the same time), or having a ring formed by $R^2$ and $R^3$ in combination, is more preferable. A particularly preferable compound is that having a hydrogen for $R^1$, a methoxy group, ethoxy group, or hydrogen for $R^2$ or $R^3$ (provided that $R^2$ and $R^3$ must not be hydrogen at the same time), or a methylenedioxy group as a ring formed by $R^2$ and $R^3$ in combination.

The present invention relates to an anti-AIDS medicine comprising one of these novel dipeptide compounds or a pharmaceutically acceptable salt thereof as an effective component.

The dipeptide compound of the present invention is a hydroxymethylcarboxamide derivative, which is an α-aminocarboxamide containing a 3-amino-2-hydroxy-4-substituted-phenylbutanoyl skeleton and a five-membered ring connected via an amide bond, as a substrate transition state mimetic structure essential for HIV protease inhibition activity. In the dipeptide compound of the present invention, if the 3-amino-2-hydroxy-4-substituted-phenylbutanoyl skeleton is provided with a (2S, 3S) steric configuration and the α-aminocarboxamide containing a five-membered ring has a steric configuration in which the corresponding α-amino acid is an (L)-isomer, such a compound exhibits particularly high HIV protease inhibition activity.

As examples of the linear or branched, saturated or unsaturated lower alkyl group, alkoxyl group, alkyl amino group, or dialkyl amino group having 1–4 carbon atoms (with a carbon atom being either replaced by an oxygen atom or not), represented by $R^1$, $R^2$, and $R^3$ in the above formula (I) or (II), the following groups can be given: methyl group, ethyl group, propyl group, butyl group, isopropyl group, sec-butyl group, tert-butyl group, vinyl group, allyl group, isopropenyl group, 1-propenyl group, methoxy group, ethoxy group, propoxy group, butoxy group, isopropoxy group, sec-butoxy group, tert-butoxy group, vinyloxy group, allyloxy group, isopropenyloxy group, 1-propenyloxy group, methoxymethoxy group, ethoxymethoxy group, methoxyethoxy group, methylamino group, ethylamino group, propylamino group, dimethylamino group, and diethylamino group. As halogeno groups, fluoro group, chloro group, and bromo group can be given. As cyclic compound formed by $R^2$ and $R^3$, a methylenedioxy group, ethylenedioxy group, ethylene group, and the like can be given. Of these groups, lower alkoxy groups such as a methoxy group, ethoxy group, propoxy group, butoxy group, isopropoxy group, and methylenedioxy group are preferable, with particularly preferable groups being a methoxy group, ethoxy group, and methylenedioxy group.

As examples of the linear or branched lower alkyl group having 1–4 carbon atoms represented by $R^4$ in the above formula (I) or (II), a methyl group, ethyl group, propyl group, butyl group, isopropyl group, and sec-butyl group can be given. A methyl group is particularly preferable group.

X in the above formula (I) or (II) is a methylene group or a sulfur atom. The sulfur atom may be present as a thio group, sulfinyl group, or sulfonyl group.

As the α-amino acid residue consisting of the five-membered ring containing the groups represented by X and $R^4$, proline, 3,3-dimethylpyrrolidine-2-carboxylic acid, 1,3-thiazolidine-4-carboxylic acid, 5,5-dimethyl-1,3-thiazolidine-4-carboxylic acid, and the like can be given, with 5,5-dimethyl-1,3-thiazolidine-4-carboxylic acid being particularly preferable.

As examples of the five-membered or six-membered monocyclic hydrocarbon group, polycyclic hydrocarbon group, or heterocyclic group derived from the monocyclic or polycyclic hydrocarbon group by replacing one or more carbon atom with a hetero atom, represented by Y in the above formula (I) or (II), the following groups can be given: phenyl group, 1-naphthyl group, 2-naphthyl group, phenylphenyl group, methylphenyl group, dimethylphenyl group, trimethylphenyl group, ethylphenyl group, methylethylphenyl group, diethylphenyl group, triethylphenyl group, propylphenyl group, dipropylphenyl group, butylphenyl group, pentylphenyl group, hexylphenyl group, cyclohexylphenyl group, fluorophenyl group, chlorophenyl group, bromophenyl group, difluorophenyl group, dichlorophenyl group, dibromophenyl group, chlorofluorophenyl group, trifluorophenyl group, trichlorophenyl group, fluoromethylphenyl group, trifluoromethylphenyl group, tetrahydrofuranyl group, tetrahydropyranyl group, furfuryl group, benzofurfuryl group, thienyl group, benzothienyl group, pyrrolyl group, imidazoyl group, pyridyl group, pyrimidyl group, pyridazyl group, pyrazyl group, tetrazinyl group, quinolyl group, isoquinolyl group, and pyridyl methyl group.

The following can be given as examples of the aryloxyalkyl group having 12 or less carbon atoms, in which the aromatic ring may be substituted with an alkyl group, alkoxy group, or halogeno group:phenoxymethyl group, methylphenoxy methyl group, dimethylphenoxymethyl group, trimethylphenoxymethyl group, ethylphenoxymethyl group, diethylphenoxymethyl group, triethylphenoxymethyl group, chlorophenoxymethyl group, dichlorophenoxymethyl group, trichlorophenoxymethyl group, fluorophenoxymethyl group, difluorophenoxymethyl group, trifluorophenoxymethyl group, trifluoromethylphenoxymethyl group, methoxyphenoxymethyl group, dimethoxyphenoxymethyl group, and trimethoxyphenoxymethyl group.

The compound in which Y is the group represented by the formula (III) or (IV) is preferable; provided that in the formula (III), $R^5$ indicates a linear or branched lower alkyl group having 1–4 carbon atoms or a halogeno group, $R^6$ is an amino group or hydroxyl group, and $R^7$, $R^8$ and $R^9$ individually represent a hydrogen, methyl group, or fluoro group, and in the formula (IV), $R^{10}$–$R^{14}$ individually represent a linear or branched lower alkyl or alkoxy group having 1–4 carbon atoms, halogeno group, amino group, hydroxyl group, or hydrogen.

As examples of the linear or branched lower alkyl group having 1–4 carbon atoms, or the halogeno group represented by $R^5$ in the formula (III), a methyl group, ethyl group, propyl group, butyl group, isopropyl group, sec-butyl group, fluoro group, chloro group, and bromo group can be given. Of these, methyl group, ethyl group, choro group, and bromo group are preferable, with methyl group and choro group being particularly preferable.

$R^7$, $R^8$, and $R^9$ in the formula (III) individually represent a hydrogen, a methyl group, or a fluoro group, with hydrogen or fluoro group being particularly preferable.

As specific examples of the group Y in the formula (III), of which preferable substituents are selected from the groups given for $R^5$ to $R^9$, 3-hydroxy-2-methylphenyl group, 2-ethyl-3-hydroxyphenyl group, 3-amino-2-methylphenyl group, 3-amino-2-ethylphenyl group, 3-amino-2-chlorophenyl group, and 2-chloro-3-hydroxyphenyl group, with 3-hydroxy-2-methylphenyl group, 3-amino-2-methylphenyl group, 3-amino-2-chlorophenyl group, and 2-chloro-3-hydroxyphenyl group being particularly preferable.

As examples of the linear or branched lower alkyl or alkoxyl group having 1–4 carbon atoms, halogeno group, or hydrogen represented by $R^{10}$–$R^{14}$ in the formula (IV), a methyl group, ethyl group, propyl group, butyl group, isopropyl group, sec-butyl group, fluoro group, chloro group, bromo group, methoxy group, ethoxy group, propoxy group, butoxy group, isopropoxy group, sec-butoxy group, tert-butoxy group, and hydrogen can be given. Of these, methyl group, fluoro group, choro group, and hydrogen are preferable. Particularly preferable selection is a methyl group for $R^{10}$ and $R^{14}$ and hydrogen atom for $R^{11}$–$R^{13}$, or a methyl group for $R^{10}$, $R^{12}$, and $R^{14}$ and hydrogen for $R^{11}$ and $R^{13}$.

Examples of the aliphatic hydrocarbon group having 1–6 carbon atoms or aromatic hydrocarbon group having 12 or less carbon atoms in which the aromatic ring may be substituted with an alkyl group, alkoxy group, or halogeno group or one or more carbon atoms in the aromatic hydrocarbon group may be replaced by hetero atoms include:phenyl group, 1-naphthyl group, 2-naphthyl group, phenylphenyl group, methylphenyl group, dimethylphenyl group, trimethylphenyl group, ethylphenyl group, methylethylphenyl group, diethylphenyl group, propylphenyl group, dipropylphenyl group, butylphenyl group, pentylphenyl group, hexylphenyl group, cyclopentylphenyl group, cyclohexylphenyl group, fluorophenyl group, chlorophenyl group, bromophenyl group, difluorophenyl group, dichlorophenyl group, dibromophenyl group, chlorofluorophenyl group, trifluorophenyl group, trichlorophenyl group, fluoromethylphenyl group, trifluoromethylphenyl group, benzyl group, 1-phenethyl group, 2-phenethyl group, phenylpropyl group, phenylbutyl group, phenylpentyl group, phenylhexyl group, methylbenzyl group, 1-methylphenethyl group, dimethylbenzyl group, dimethylphenethyl group, trimethylbenzyl group, ethylbenzyl group, diethylbenzyl group, chlorobenzyl group, dichlorobenzyl group, fluorobenzyl group, difluorobenzyl group, trifluorobenzyl group, chloromethylbenzyl group, fluoromethylbenzyl group, methoxybenzyl group, dimethoxybenzyl group, ethoxybenzyl group, diethoxybenzyl group, piperonylbenzyl group, 1-indanyl group, and 2-indanyl group.

As the aliphatic hydrocarbon groups having 1–6 carbon atoms, a methyl group, ethyl group, propyl group, isopropyl group, butyl group, isobutyl group, sec-butyl group, tert-butyl group, pentyl group, hexyl group, and the like are preferable. Excellent results can be expected when a branched alkyl group having 3–5 carbon atoms such as a tert-butyl group is selected.

Given as preferable examples of the aromatic hydrocarbon group having 12 or less carbon atoms in which the aromatic ring may be substituted with an alkyl group, alkoxy group, or halogeno group, or one or more carbon atoms in the aromatic hydrocarbon group may be replaced by hetero atoms, represented by Z in the formula (I) or (II) are compounds shown by the formula (V), wherein $R^{15}$–$R^{19}$ individually represent a linear or branched lower alkyl or alkoxy group having 1–4 carbon atoms, a halogeno group, or a hydrogen atom. Specific examples of the linear or branched lower alkyl or alkoxy group having 1–4 carbon atoms or the halogeno group represented by $R^{15}$–$R^{19}$ in the formula (V) include: methyl group, ethyl group, propyl group, butyl group, isopropyl group, sec-butyl group, methoxy group, ethoxy group, propoxy group, butoxy group, isopropoxy group, sec-butoxy group, tert-butoxy group, fluoro group, chloro group, and bromo group. More preferable selection is a methyl or chloro group for $R^{15}$, a hydrogen, methyl, or fluoro group for $R^{16}$–$R^{19}$, and particularly a methyl group for $R^{15}$ and a hydrogen or fluoro group for $R^{16}$–$R^{18}$, or a methyl group for $R^{15}$ and $R^{19}$ and a hydrogen or fluoro group for $R^{16}$–$R^{18}$.

Specific examples of particularly preferable compounds of the present invention include, but are not limited to the following compounds: (R)-N-(2-methylbenzyl)-3-[(2S,3S)-2-hydroxy-3-(3-hydroxy-2-methylbenzoyl)amino-4-(4-methoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(4-methoxyphenyl)butanoyl]-5,5-dimethyl-1,3-thiazolidine-4- carboxamide, (R)-N-(2,6-dimethylbenzyl)-3-[(2S,3S)-2-hydroxy-3-(3-hydroxy-2-methylbenzoyl)amino-4-(4-methoxyphenyl)butanoyl]-5,5-dimethyl-1,3-thiazolidine-4-carboxamide, (R)-N-(2,6-dimethylbenzyl-3-[(2S,3S)-2-hydroxy-3-(3-amino-2-chlorobenzoyl)amino-4-(4-methoxyphenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(3-methoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(3-methoxyphenyl)butanoyl]-5,5-dimethyl-1,3-thiazolidine-4-carboxamide, (R)-N-(2,6-dimethylbenzyl-3-[(2S,3S)-2-hydroxy-3-(3-hydroxy-2-methylbenzoyl)amino-4-(3-methoxyphenyl)butanoyl]-5,5-dimethyl-1,3-thiazolidine-4-carboxamide, (R)-N-(2,6-dimethylbenzyl-3-[(2S,3S)-2-hydroxy-3-(3-amino-2-chlorobenzoyl)amino-4-(3-methoxyphenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(4-ethoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(4-ethoxyphenyl)butanoyl]-5,5-dimethyl-1,3-thiazolidine-4-carboxamide, (R)-N-(2,6-dimethylbenzyl-3-[(2S,3S)-2-hydroxy-3-(3-hydroxy-2-methylbenzoyl)amino-4-(4-ethoxyphenyl)butanoyl]-5,5-dimethyl-1,3-thiazolidine-4-carboxamide, (R)-N-(2,6-dimethylbenzyl)-3-[(2S,3S)-2-hydroxy-3-(3-amino-2-chlorobenzoyl)amino-4-(4-ethoxyphenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(3,4-methylenedioxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(3,4-methylenedioxyphenyl)butanoyl]-5,5-dimethyl-1,3-thiazolidine-4-carboxamide, (R)-N-(2,6-dimethylbenzyl)-3-[(2S,3S)-2-hydroxy-3-(3-hydroxy-2-methylbenzoyl)amino-4-(3,4-methylenedioxyphenyl) -butanoyl]-5,5-dimethyl-1,3-thiazolidine-4-carboxamide, (R)-N-(2,6-dimethylbenzyl)-3-[(2S,3S)-2-hydroxy-3-(3-amino-2-chlorobenzoyl)amino-4-(3,4-methylenedioxyphenyl) -butanoyl]-5,5-Dimethyl-1-3-thiazolidine-4-carboxamide, (R)-N-(2-methylbenzyl)-3-[(2S,3S)-2-hydroxy-3-(3-hydroxy-2-methylbenzoyl)amino-4-(4-propoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(4-propoxyphenyl)butanoyl]-5,5-dimethyl-1,3-thiazolidine-4-carboxamide, (R)-N-(2,6-dimethylbenzyl-3-[(2S,3S)-2-hydroxy-3-(3-hydroxy-2-methylbenzoyl)amino-4-(4-propoxyphenyl)butanoyl]-5,5-dimethyl-1,3-thiazolidine-4-carboxamide, (R)-N-(2,6-dimethylbenzyl-3-[(2S,3S)-2-hydroxy-3-(3-amino-2-chlorobenzoyl)amino-4-(4-propoxyphenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(4-isopropoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(4-isopropoxyphenyl)butanoyl]-5,5-dimethyl-1,3-thiazolidine-4-carboxamide, (R)-N-(2,6-dimethylbenzyl-3-[(2S,3S)-2-hydroxy-3-(3-hydroxy-2-methylbenzoyl)amino-4-(4-isopropoxyphenyl) butanoyl]-5-,5-dimethyl-1,3-thiazolidine-4-carboxamide, (R)-N-(2,6-dimethylbenzyl-3-[(2S,3S)-2-hydroxy-3-(3-amino-2-chlorobenzoyl)amino-4-(4-isopropoxyphenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(3,4-dimethoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(3,4-dimethoxyphenyl)butanoyl]-5,5-dimethyl-1,3-thiazolidine-4-carboxamide, (R)-N-(2,6-dimethylbenzyl-3-[(2S,3S)-2-hydroxy-3-(3-hydroxy-2-methylbenzoyl)amino-4-(3,4-dimethoxyphenyl) -butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(3,5-dimethoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(3,5-dimethoxyphenyl)butanoyl]-5,5-dimethyl-1,3-thiazolidine-4-carboxamide, (R)-N-(2,6-dimethylbenzyl-3-[(2S,3S)-2-hydroxy-3-(3-hydroxy-2-methylbenzoyl)amino-4-(3,4-dimethoxyphenyl) -butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(3,4,5-trimethoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(3,4,5-trimethoxyphenyl)butanoyl]-5,5-dimethyl-1,3-thiazolidine-4-carboxamide, (R)-N-(2,6-dimethylbenzyl)-3-[(2S,3S)-2-hydroxy-3-(3-hydroxy-2-methylbenzoyl)amino-4-(3,4,5-trimethoxyphenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(4-chlorophenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(4-chlorophenyl)butanoyl]-5,5-dimethyl-1,3-thiazolidine-4-carboxamide, (R)-N-(2,6-dimethylbenzyl)-3-[(2S,3S)-2-hydroxy-3-(3-hydroxy-2-methylbenzoyl)amino-4-(4-chlorophenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(3-chlorophenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(3-chlorophenyl)butanoyl]-5,5-dimethyl-1,3-thiazolidine-4-carboxamide, (R)-N-(2,6-dimethylbenzyl)-3-[(2S,3S)-2-hydroxy-3-(3-hydroxy-2-methylbenzoyl)amino-4-(3-chlorophenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(4-fluorophenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(4-fluorophenyl)butanoyl]-5,5-dimethyl-1,3-thiazolidine-4-carboxamide, (R)-N-(2,6-dimethylbenzyl)-3-[(2S,3S)-2-hydroxy-3-(3-hydroxy-2-methylbenzoyl)amino-4-(4-fluorophenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(3-fluorophenyl)butanoyl]-5,5-dimethyl-1-3-thiazolidine-4-carboxamide, (R)-N-(2-methylbenzyl)-3-[(2S,3S)-2-hydroxy-3-(3-amino-2-chlorobenzoyl)amino-4-(3-fluorophenyl)butanoyl]-5,5-dimethyl-1,3-thiazolidine-4-carboxamide, (R)-N-(2,6-dimethylbenzyl)-3-[(2S,3S)-2-hydroxy-3-(3-hydroxy-2-methylbenzoyl)amino-4-(3-fluorophenyl)butanoyl]-5,5-dimethyl-1,3-thiazolidine-4-carboxamide, (R)-N-(2-methylbenzyl)-3-[(2S,3S)-2-hydroxy-3-(3-hydroxy-2-methylbenzoyl)amino-4-(4-methylphenyl)butanoyl]-5,5-dimethyl-1,3-thiazolidine-4-carboxamide, (R)-N-(2-methylbenzyl)-3-[(2S,3S)-2-hydroxy-3-(3-amino-2-chlorobenzoyl)amino-4-(4- methylphenyl)butanoyl]-5,5-dimethyl-1,3-thiazolidine-4-carboxamide, (R)-N-(2,6-dimethylbenzyl)-3-[(2S,3S)-2-hydroxy-3-(3-hydroxy-2-methylbenzoyl)amino-4-(4-methylphenyl)butanoyl]-5,5-dimethyl-1,3-thiazolidine-4-carboxamide, (R)-N-(5-fluoro-2-methylbenzyl)-3-[(2S,3S)-2-hydroxy-3-(4-fluoro-3-hydroxy-2-methylbenzoyl)amino-4-(4-methoxyphenyl)butanoyl]-5,5-dimethyl-1,3-thiazolidine-4-carboxamide, (R)-N-(2-methylbenzyl)-3-[(2S,3S)-2-hydroxy-3-(4-fluoro-3-hydroxy-2-methylbenzyl)amino-4-(4-methoxyphenyl)butanoyl]-5,5-dimethyl-1,3-thiazolidine-4-carboxamide, (R)-N-(5-fluoro-2-methylbenzyl)-3-[(2S,3S)-2-hydroxy-3-(3-amino-2-chlorobenzoyl)amino-4-(4-methoxyphenyl)butanoyl]-5,5-dimethyl-1,3-thiazolidine-4-carboxamide, (R)-N-(tert-butyl)-3-[(2S,3S)-2-hydroxy-3-(3-hydroxy-2-methylbenzoyl)amino-4-(4-methoxyphenyl)butanoyl]-5,5-dimethyl-1,3-thiazolidine-4-carboxamide, (R)-N-(tert-butyl)-3-[(2S,3S)-2-hydroxy-3-(3-amino-2-chlorobenzoyl)amino-4-(4-methoxyphenyl)butanoyl]-5,5-dimethyl-1,3-thiazolidine-4-carboxamide, (R)-N-(tert-butyl)-3-[(2S,3S)-2-hydroxy-3-(2,6-dimethylphenoxyacetyl)amino-4-(4-methoxyphenyl)butanoyl]-5,5-dimethyl-1,3-thiazolidine-4-carboxamide, (R)-N-(tert-butyl)-3-[(2S,3S)-2-hydroxy-3-(3-hydroxy-2-methylbenzoyl)amino-4-(4-ethoxyphenyl)butanoyl]-5,5-dimethyl-1,3-thiazolidine-4-carboxamide, (R)-N-(tert-butyl)-3-[(2S,3S)-2-hydroxy-3-(3-amino-2-chlorobenzoyl)amino-4-(4-ethoxyphenyl)butancyl]-5,5-dimethyl-1,3-thiazolidine-4-carboxamide, (R)-N-(tert-butyl)-3-[(2S,3S)-2-hydroxy-3-(2,6-dimethylphenoxyacetyl)amino-4-(4-ethoxyphenyl)butanoyl]-5,5-dimethyl-1,3-thiazolidine-4-carboxamide, (R)-N-(tert-butyl)-3-[(2S,3S)-2-hydroxy-3-(3-hydroxy-2-methylbenzoyl)amino-4-(3,4-methylenedioxyphenyl)butanoyl]-5,5-dimethyl-1,3-thiazolidine-4-carboxamide, (R)-N-(tert-butyl)-3-[(2S,3S)-2-hydroxy-3-(3-amino-2-chlorobenzoyl)amino-4-(3,4-methylenedioxyphenyl)butanoyl]-5,5-dimethyl-1,3-thiazolidine-4-carboxamide, (R)-N-(tert-butyl)-3-[(2S,3S)-2-hydroxy-3-(2,6-dimethylphenoxyacetyl)amino-4-(3,4-methylenedioxyphenyl) -butanoyl]-5,5-dimethyl-1,3-thiazolidine-4-carboxamide, (R)-N-(tert-butyl)-3-[(2S,3S)-2-hydroxy-3-(3-hydroxy-2-methylbenzoyl)amino-4-(4-propoxyphenyl)butanoyl]-5,5-dimethyl-1,3-thiazolidine-4-carboxamide, (R)-N-(tert-butyl)-3-[(2S,3S)-2-hydroxy-3-(3-amino-2-chlorobenzoyl)amino-4-(4-propoxyphenyl)butanoyl]-5,5-dimethyl-1,3-thiazolidine-4-carboxamide, (R)-N-(tert-butyl)-3-[(2S,3S)-2-hydroxy-3-(2,6-dimethylphenoxyacetyl)amino-4-(4-propoxyphenyl)butanoyl]-5,5-dimethyl-1,3-thiazolidine-4-carboxamide, (R)-N-(tert-butyl)-3-[(2S,3S)-2-hydroxy-3-(3-hydroxy-2-methylbenzoyl)amino-4-(4-isopropoxyphenyl)butanoyl]-5,5-dimethyl-1,3-thiazolidine-4-carboxamide, (R)-N-(tert-butyl)-3-[(2S,3S)-2-hydroxy-3-(3-amino-2-chlorobenzoyl)amino-4-(4-isopropoxyphenyl)butanoyl]-5,5-dimethyl-1,3-thiazolidine-4-carboxamide, (R)-N-(tert-butyl)-3-[(2S,3S)-2-hydroxy-3-(2,6-dimethylphenoxyacetyl)amino-4-(4-isopropoxyphenyl) -butanoyl]-5,5-dimethyl-1,3-thiazolidine-4-carboxamide, (R)-N-(2-methylbenzyl)-3-[(2S,3S)-2-hydroxy-3-(3-amino-2-methylbenzoyl)amino-4-(4-methoxyphenyl)butanoyl]-5,5-dimethyl-1,3-thiazolidine-4-carboxamide, (R)-N-(2,6-dimethylbenzyl)-3-[(2S,3S)-2-hydroxy-3-(3-amino-2-methylbenzoyl)amino-4-(4-methoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-methylbenzoyl)amino-4-(4-ethoxyphenyl)butanoyl]-5,5-dimethyl-1,3-thiazolidine-4-carboxamide, (R)-N-(2,6-dimethylbenzyl-3-[(2S,3S)-2-hydroxy-3-(3-amino-2-methylbenzoyl)amino-4-(4-ethoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-methylbenzoyl)amino-4-(4-isopropoxyphenyl)butanoyl]-5,5-dimethyl-1,3-thiazolidine-4-carboxamide, (R)-N-(2,6-dimethylbenzyl-3-[(2S,3S)-2-hydroxy-3-(3-amino-2-methylbenzoyl)amino-4-(4-isopropoxyphenyl)butanoyl]-5,5-dimethyl-1,3-thiazolidine-4-carboxamide, (R)-N-(2-methylbenzyl)-3-[(2S,3S)-2-hydroxy-3-(3-amino-2-methylbenzoyl)amino-4-(3,4-methylenedioxyphenyl)butanoyl]5,5-dimethyl-1,3-thiazolidine-4-carboxamide, (R)-N-(2,6-dimethylbenzyl-3-[(2S,3S)-2-hydroxy-3-(3-amino-2-methylbenzoyl)amino-4-(3,4-methylenedioxyphenyl) -butanoyl]-5,5-Dimethyl-1-3-thiazolidine-4-carboxamide, (R)-N-(2-methylbenzyl)-3-[(2S,3S)-2-hydroxy-3-(2,6-dimethylphenoxyacetyl)amino-4-(4-methoxyphenyl)butanoyl]-5,5-dimethyl-1,3-thiazolidine-4-carboxamide, (R)-N-(2,6-dimethylbenzyl)-3-[(2S,3S)-2-hydroxy-3-(2,6-dimethylphenoxyacetyl)amino-4-(4-methoxyphenyl)butanoyl]-5,5-dimethyl-1,3-thiazolidine-4-carboxamide, (R)-N-(2-methylbenzyl)-3-[(2S,3S)-2-hydroxy-3-(2,6-dimethylphenoxyacetyl)amino-4-(4-ethoxyphenyl)butanoyl]-5,5-dimethyl-1,3-thiazolidine-4-carboxamide, (R)-N-(2,6-dimethylbenzyl)-3-[(2S,3S)-2-hydroxy-3-(2,6-dimethylphenoxyacetyl)amino-4-(4-ethoxyphenyl)butanoyl]-5,5-dimethyl-1,3-thiazolidine-4-carboxamide, (R)-N-(2-methylbenzyl)-3-[(2S,3S)-2-hydroxy-3-(2,6-dimethylphenoxyacetyl)amino-4-(4-isopropoxyphenyl) -butanoyl]-5,5-dimethyl-1,3-thiazolidine-4-carboxamide, (R)-N-(2,6-dimethylbenzyl)-3-[(2S,3S)-2-hydroxy-3-(2,6-dimethylphenoxyacetyl)amino-4-(4-isopropoxyphenyl) -butanoyl]-5,5-dimethyl-1,3-thiazolidine-4-carboxamide, (R)-N-(2-methylbenzyl)-3-[(2S,3S)-2-hydroxy-3-(2,6-dimethylphenoxyacetyl)amino-4-(3,4-methylenedioxyphenyl) -butanoyl]-5,5-dimethyl-1,3-thiazolidine-4-carboxamide, (R)-N-(2,6-dimethylbenzyl)-3-[(2S,3S)-2-hydroxy-3-(2,6-dimethylphenoxyacetyl)amino-4-(3,4-methylenedioxyphenyl) -butanoyl]-5,5-dimethyl-1,3-thiazolidine-4-carboxamide.

Specific examples of the pharmaceutically acceptable salt of dipeptide compound of the present invention include a hydrochloride, acetate, methanesulfonate, oxalate, citrate, and succinate.

The dipeptide compounds shown by the above formula (I) or (II) can be easily prepared using a known method of synthesizing α-hydroxy-β-amino acid (R. Nishizawa, et al., J. Med. Chem., 20, 510–515, 1977; W. Yuan et al., J. Med. Chem., 36, 211–220, 1993; Matsumoto et al., Japanese Patent Application Laid-open No. 10-59909; or Suzuki et al., Japanese Patent Application Laid-open No. 9-157247), and a known method of synthesizing a hydroxymethylcarboxamide-type HIV protease inhibitor (T. Mimoto et al. J. Med. Chem., 42, 1789–1802, 1999, etc.).

For example, an aminoaldehyde derivative (in which the amino group is protected) is prepared by a conventional method and reacted with hydrogen cyanide or its equivalent to produce a cyanhydrin derivative, which is hydrolyzed under acidic conditions, for example, in the presence of hydrochloric acid, thereby obtaining the target α-hydroxy-β-amino acid. Alternatively the α-hydroxy-β-amino acid can be prepared by hydrolyzing α-amino-β', α'-dihaloketone derivatives, prepared by a conventional method, in the presence of a base. In this instance, the product which is predominantly obtained is a more preferable steric isomer (2S,3S). The resultant α-hydroxy-β-amino acids can be converted into amino-protected α-hydroxy-β-amino acid derivatives by the reaction with a commonly used amino group protecting reagent such as Boc$_2$O or Z-Cl in the presence of an organic base such as triethylamine or a mineral base such as sodium hydroxide. Thus obtained amino-protected α-hydroxy-β-amino acids can be recrystallized or formed to ester-derivative and then separated using column chromatography, thereby obtaining the derivative containing only (2S, 3S) derivative which is more preferable.

On the other hand, the hydroxymethylcarboxamide compound can be synthesized, for example, by following procedure.

An α-aminocarboxamide derivative, which has a substituted benzyl group on the nitrogen atom of its carbamoyl group, is condensed with an amino-protected (2S,3S)-3-amino-2-hydroxy-4-substituted-phenylbutanoic acid using a carbodiimide reagent (e.g DCC (N,N'-dicyclohexylcarbodiimide), EDC (1-ethyl-3-(3-N,N'-dimethylaminopropyl)carbodiimide), etc.) in the presence of additives (HOBt (N-hydroxybenzotriazole), HOSu (N-hydroxysuccinimide), and the like), then deprotecting the amino group by using an acid such as hydrochloric acid or by catalytic hydrogenation using a Pd catalyst. The dipeptide of present invention is obtained by reacting the resulting dipeptide amine derivative with a desired amino-modified carboxylic group activated by the acid chloride method, the mixed anhydride method (diphenyl phosphoryl chloride, and the like), or the above-mentioned carbodiimide method.

The target compound may also be synthesized by following process.

First synthesize a dipeptide derivative protected with an appropriate protecting group such as an acetyl group on the hydroxyl group or amino group of R$^5$ in the above formula (I) or (II). Then deprotect using an acid or alkali.

As required, impurities are removed by a suitable means such as column chromatography, recrystallization, and the like, and resulting purified compound can be used as an HIV protease inhibitor. The structure of dipeptide compound of the present invention can be easily determined by the NMR method, spectrophotometric method such as IR absorption, or mass spectrometry, with reference to the structure originating from raw material compounds.

The dipeptide compound of the present invention exhibits high HIV protease inhibitory activity. Because of this characteristics, the compound can become the compound which exhibits anti-virus activity by blocking formation and maturation of infective viral particles in HIV T-lymphocytes. Therefore, the compound is useful in pharmaceutical application as an anti-AIDS agent due to this effect of blocking formation and maturation of infective viral particles.

When applying the dipeptide compound of the present invention to clinical application as an anti-AIDS medicine, the compound may be administered as compounding of medicine prepared according to a conventional method by using conventional pharmaceutical substances and vehicles. Specifically, the compound may be non-orally administered as intravenous or intramuscular injection, spray, or suppository, or orally administered as granules, capsules, fluid, tablets. Because the dipeptide compound of the present invention is a low molecular compound with excellent in vivo stability and superior gastrointestinal absorption, oral administration as granules, capsules, fluid, tablets, or the like is appropriate for the compound. Although a dose is determined according to symptoms of the patients, the therapeutic objective such as suppression of AIDS symptom, control of AIDS progress, the age and sex of the patients, and the like, an approximate range is between 10 mg and 2 g per dose for adults who are administered 1–4 times a day.

DESCRIPTION OF PREFERRED EMBODIMENT OF THE INVENTION

Figure 1:
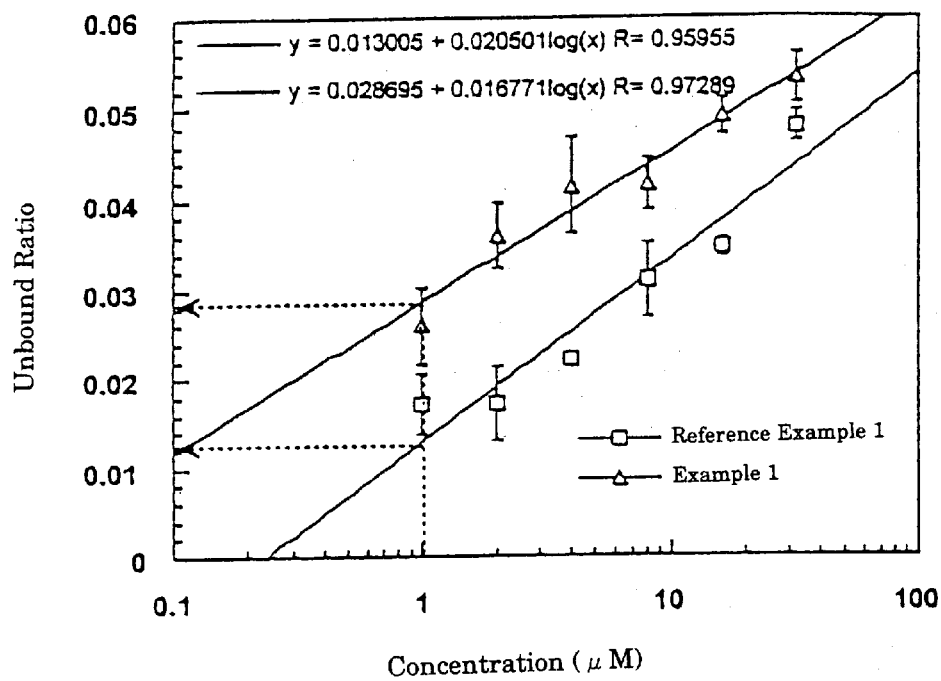
FIG. 1 shows the unbound ratio of the compounds of Example 1 and Reference Example 1 to human plasma, plotted against the concentration of the compound.

The present invention will be described in more detail by examples and reference examples, which are not intended to be limiting of the present invention.

EXAMPLES

The method of preparing the dipeptide compound and the salt thereof of the present invention will now be specifically described.

In the Examples, Dmt stands for (R)-5,5-dimethyl-1,3-thiazolidine-4-carbonyl; Apns, (2S,3S)-3-amino-2-hydroxy-4-phenylbutanoyl; Apns(4-OMe), (2S,3S)-3-amino-2-hydroxy-4-(4-methoxyphenyl)butanoyl; Boc, tert-butoxycarbonyl; TEA, triethylamine; and DPP-Cl, diphenylphosphoryl chloride.

Example 1
(R)-N-(2-methylbenzyl)-3-[(2S,3S)-2-hydroxy-3-(3-hydroxy-2-methylbenzoyl)amino-4-(4-methoxyphenyl)butanoyl]-5,5-dimethyl-1,3-thiazolidine-4-carboxamide
Step 1
(R)-N-(2-methylbenzyl)-5,5-dimethyl-1,3-thiazolidine-4-carboxamide DPP-Cl (4.55 ml) was added to a solution of Boc-Dmt-OH (5.22 g) and TEA (3.06 ml) in EtOAc (50 ml) while cooling with ice, and the mixture was stirred for one hour. After the addition of 2-methylbenzylamine (2.73 ml) and TEA (3.06 ml), the mixture was stirred overnight. The reaction mixture was washed with 5% Na$_2$CO$_3$ (×2), 1N HCl, and 5% NaCl, and dried over MgSO$_4$. After filtration and concentration, the residue obtained was dissolved in CH$_2$Cl$_2$, followed by the addition of 4N HCl/Dioxane (30 ml). The solution was stirred for one hour and concentrated. The residue was dissolved in water, washed with toluene, neutralized with 2N NaOH while cooling with ice, extracted with EtOAc, and dried over MgSO$_4$. After filtration and concentration, the residue was recrystallized from a mixture of EtOAc and n-hexane to obtain the title compound (3.75 g, 71%). $^1$H NMR (DMSO-d6) δ (ppm); 1.15 (s, 3H), 1.52 (s, 3H), 2.28 (s, 3H), 3.27 (s, 1H), 3.66 (br, 1H), 4.03 (d, 1H, J=9.6 Hz), 4.22–4.33 (m, 3H), 7.12–7.22 (m, 4H), 8.32–8.33 (br, 1H):
Step 2
(R)-N-(2-methylbenzyl)-3-[(2S,3S)-3-amino-2-hydroxy-4-(4-methoxyphenyl)butanoyl]-5,5-dimethyl-1,3-thiazolidine-4-carboxamide Boc-Apns (4-OMe)-OH (1.14 g), HOBt-H$_2$O (0.54 g), and DCC (0.83 g) were added to a solution of the compound obtained in Step 1 (0.97 g) in EtOAc (37 ml), and the mixture was stirred overnight. The reaction mixture was filtered, washed with 5% Na$_2$CO$_3$ (×2), 1N HCl, and 5% NaCl, and dried over MgSO$_4$. After filtration and concentration, the residue was added with 4N HCl/dioxane (10 ml) and the mixture was stirred for one hour and concentrated. The residue was dissolved in water, filtered, and adjusted to pH 10 by the addition of 3N NaOH, followed by crystallization and filtration. The crystals were dried, and recrystallized from a mixture of EtOAc and n-hexane to obtain the title compound (1.23 g, 75%). $^1$H NMR (DMSO-$d_6$) δ (ppm); 1.15–1.25 (br, 2H), 1.33 (s, 3H), 1.52 (s, 3H), 2.17 (s, 3H), 2.2–2.3 (m, 1H), 2.64 (t, 1H, J=8.0 Hz), 3.02 (d, 1H, J=13.2 Hz), 3.74 (s, 3H), 4.02–4.09 (br, 1H), 4.14 (d, 1H, J=4.9 Hz), 4.20 (d, 1H, J=4.9 Hz), 4.36 (s, 1H), 4.90 (s, 2H), 5.30 (d, 1H, J=7.8 Hz), 6.95 (s, 3H), 6.86 (d, 2H, J=8.6 Hz), 6.94–7.15 (m, 6H), 8.55 (t, 1H, J=5.1 Hz):

Step 3
(R)-N-(2-methylbenzyl)-3-[(2S,3S)-2-hydroxy-3-(3-hydroxy-2-methylbenzoyl)amino-4-(4-methoxyphenyl)butanoyl]3-5,5-dimethyl-1,3-thiazolidine-4-carboxamide DPP-Cl(84 μl) and TEA(57 μl) were added to a solution of 3-acetoxy-2-methylbenzoic acid (79 mg) in EtOAc (2 ml), and the mixture was stirred for one hour. After the addition of the compound obtained in Step 2 (174 mg) and TEA (62 μl), the mixture was stirred overnight. The reaction mixture was washed with 5% $Na_2CO_3$ (×2), 1N HCl, and 5% NaCl. After concentration, MeOH (1.5 ml)and 1N NaOH (0.75 ml) were added. After stirring for one hour, 1N HCl was added to make the reaction mixture acidic. The resulting mixture was extracted with EtOAc. The extract was washed with 5% $Na_2CO_3$ (×2), 1N HCl, and 5% NaCl, and dried over $MgSO_4$. After filtration and concentration, the residue was recrystallizied from a mixture of EtOAc and n-hexane to obtain the title compound (176 mg, 79%).
HPLC: 21.49 min
HPLC conditions:
  Column, YMC AS-302, φ 4.6×150 mm
  Eluate: 0.1% aqueous solution of trifluoroacetic acid /acetonitrile;
  Elution conditions: 0–100% linear concentration gradient (30 min);
  Flow rate: 1 ml/min.
(the same conditions apply to HPLC in the following experiments)
$^1$H NMR (DMSO-d6) δ (ppm); 1.35 (s, 3H, Dmt-5-$CH_3$), 1.50 (s, 3H, Dmt-5-$CH_3$), 1.83 (s, 3H, benzoyl-$CH_3$), 2.26 (s, 3H, benzylamine-$CH_3$), 2.6–2.8 (m, 2H, Apns-4-$CH_2$), 3.70 (s, 3H, Apns-$OCH_3$), 4.09 (dd, 1H, J=5.1 Hz, 15.1 Hz, benzylamine-$CH_2$), 4.3–4.5 (m, 4H, benzylamine-$CH_2$, Dmt-4-CH, Apns-2-CH, and Apns-3-CH), 5.01 (d, 1H, J=9.5 Hz, Dmt-2-$CH_2$), 5.13 (d, 1H, J=8.6 Hz, Dmt-2-$CH_2$), 5.45 (d, 1H, J=6.8 Hz, Apns-2-OH), 6.58 (d, 1H, J=7.0 Hz, aromatic), 6.7–6.9 (m, 3H, aromatic), 6.96 (t, 1H, J=7.8 Hz, aromatic), 7.0–7.4 (m, 6H, aromatic), 8.11 (d, 1H, J=8.1 Hz, Apns-NH), 8.32 (t, 1H, J=5.4 Hz, benzylamine-NH), 9.40 (s, 1H, benzoyl-OH);
MS(TOF) m/z=607($M^+$+H)

Example 2
(R)-N-(5-fluoro-2-methylbenzyl)-3-[(2S,3S)-2-hydroxy-3-(3-hydroxy-2-methyl-benzoyl)amino-4-(4-methoxyphenyl)butanoyl]-5,5-dimethyl-1,3-thiazolidine-4-carboxamide
Step 1
(R)-N-(5-fluoro-2-methylbenzyl)-5,5-dimethyl-1,3-thiazolidine-4-carboxamide DPP-Cl (1.15 ml) was added to a solution of Boc-Dmt-OH (1.32 g) and TEA (0.77 ml) in EtOAc (15 ml) while cooling with ice, and the mixture was stirred for one hour. After the addition of 5-fluoro-2-methylbenzylamine hydrochloride (0.77 g) and TEA (1.62 ml), the mixture was stirred overnight. The reaction mixture was washed with 1N HCl, 5% NaCl, and 5% $Na_2CO_3$, and dried over $MgSO_4$. After filtration and concentration, 4N HCl/Dioxane (10 ml) was added. The solution was stirred for one hour and concentrated. The residue was dissolved in water, neutralized with 3N NaOH while cooling with ice, extracted with EtOAc. The organic layer was dried over $MgSO_4$, filtered and concentrated to obtain the title compound (0.47 g, 33%).
Step 2
(R)-N-(5-fluoro-2-methylbenzyl)-3-[(2S,3S)-3-amino-2-hydroxy-4-(4-methoxyphenyl)butanoyl]-5,5-dimethyl-1,3-thiazolidine-4-carboxamide Boc-Apns (4-OMe)-OH (0.30 g), HOBt-$H_2O$ (0.14 g), and DCC (0.21 g) were added to a solution of the compound obtained in Step 1 (0.36 g) in EtOAc (5 ml), and the mixture was stirred overnight. The reaction mixture was filtered and washed with 5% $Na_2CO_3$, 1N HCl, and 5% NaCl, dried over $MgSO_4$, filtered and concentrated. Then, after the addition of 4N HCl/dioxane (2.2 ml), the mixture was stirred for one hour. The reaction mixture was concentrated, dissolved in water, filtered, and adjusted to pH 10 by the addition of 3N NaOH, followed by extraction with EtOAc. The precipitate was filtered (0.25 g). The organic layer was dried over $MgSO_4$, filtered, and concentrated. The residue was recrystallized from a mixture of EtOAc and n-hexane to obtain the title compound (0.11 g, total 0.36 g, 66%).
Step 3
(R)-N-(5-fluoro-2-methylbenzyl)-3-[(2S,3S)-2-hydroxy-3-(3-hydroxy-2-methylbenzoyl)amino-4-(4-methoxyphenyl)butanoyl]-5,5-dimethyl-1,3-thiazolidine-4-carboxamide The reaction was carried out in the same manner as in Step 3 of Example 1 using the compound obtained in Step 2 (150 mg) and 3-acetoxy-2-methylbenzoic acid (53 mg). The resulting crude product was purified by silica gel column chromatography ($CH_2Cl_2$—MeOH) and reprecipitated from n-hexane to obtain the target compound (125 mg, 81%).
HPLC:21.16 min
$^1$H NMR (DMSO-d6) δ (ppm); 1.35 (s, 3H, Dmt-5-$CH_3$), 1.51 (s, 3H, Dmt-5-$CH_3$), 1.86 (s, 3H, benzoyl-$CH_3$), 2.23 (s, 3H, benzylamine-$CH_3$), 2.6–2.8 (m, 2H, Apns-4-$CH_2$), 3.69 (s, 3H, Apns-$OCH_3$), 4.06 (dd, 1H, J=4.3 Hz, 15.7 Hz, benzylamine-$CH_2$), 4.3–4.5 (m, 4H, benzylamine-$CH_2$, Dmt-4-CH, Apns-2-CH, and Apns-3-CH), 5.01 (d, 1H, J=9.5 Hz, Dmt-2-$CH_2$), 5.17 (d, 1H, J=9.5 Hz, Dmt-2-$CH_2$), 5.49 (d, 1H, J=6.8 Hz, Apns-2-OH), 6.57 (d, 1H, J=7.3 Hz, aromatic), 6.78 (d, 3H, J=8.1 Hz, aromatic), 6.9–7.0 (m, 2H, aromatic), 7.12–7.22 (m, 4H, aromatic), 8.08 (d, 1H, J=8.4 Hz, Apns-NH), 8.40 (t, 1H, J=5.5 Hz, benzylamine-NH), 9.39 (s, 1H, benzoyl-OH):
MS(TOF) m/z =624($M^+$+H)

Example 3
(R)-N-(2-methylbenzyl)-3-[(2S,3S)-2-hydroxy-3-(4-fluoro-3-hydroxy-2-methyl-benzoyl)amino-4-(4-methoxyphenyl)butanoyl]5,5-dimethyl-1,3-thiazolidine-4-carboxamide The reaction was carried out in the same manner as in Step 3 of Example 1 using the compound obtained in Step 2 of Example 1 (94 mg) and 3-acetoxy-4-fluoro-2-methylbenzoic acid (45 mg). The resulting crude product was purified by recryatallization from a mixture of EtOAc and n-hexane to obtain the target compound (84 mg, 67%).
HPLC:21.51 min
$^1$H NMR (DMSO-d6) δ (ppm); 1.35 (s, 3H, Dmt-5-$CH_3$), 1.50 (s, 3H, Dmt-5-$CH_3$), 1.92 (s, 3H, benzoyl-$CH_3$), 2.26 (s, 3H, benzylamine-$CH_3$), 2.6–2.8 (m, 2H, Apns-4-$CH_2$), 3.70 (s, 3H, Apns-$OCH_3$), 4.10 (dd, 1H, J=4.3 Hz, 15.1 Hz, benzylamine-$CH_2$), 4.3–4.5 (m, 4H, benzylamine-$CH_2$, Dmt-4-CH, Apns-2-CH, and Apns-3-CH), 5.00 (d, 1H, J=9.2

Hz, Dmt-2-CH$_2$), 5.12 (d, 1H, J=8.6 Hz, Dmt-2-CH$_2$), 5.47 (d, 1H, J=7.0 Hz, Apns-2-OH), 6.61 (dd, 1H, J=8.4 Hz, 5.4 Hz, aromatic), 6.80 (d, 2H, J=8.1 Hz, aromatic), 6.96 (t, 1H, J=5.1 Hz, aromatic), 7.00–7.14 (m, 3H, aromatic), 7.23 (d, 2H, J=8.9 Hz, aromatic), 7.28–7.31 (m, 1H, aromatic), 8.15 (d, 1H, J=8.4 Hz, Apns-NH), 8.32 (t, 1H, J=5.4 Hz, benzylamine-NH), 9.4–9.6 (br, 1H, benzoyl-OH);

MS(TOF) m/z=624(M$^+$+H)

Example 4

(R)-N-(2-methylbenzyl)-3-[(2S,3S)-2-hydroxy-3-(3-amino-2-chlorobenzoyl)amino-4-(4-methoxyphenyl)butanoyl]-5,5-dimethyl-1,3-thiazolidine-4-carboxamide DPP-Cl(68 µl) and TEA(50 µl) were added to a solution of 3-amino-2-chlorobenzoic acid (56 mg) in EtOAc (2 ml), and the mixture was stirred for one hour. After the addition of the compound obtained in Step 2 of Example 1 (141 mg) and TEA (50 µl), the mixture was stirred overnight. The reaction mixture was washed with 5% Na$_2$CO$_3$ (×2), 1N HCl, and 5% NaCl, dried over MgSO$_4$. After filtration and concentration, the residue was purified by silica gel column chromatography (CH$_2$Cl$_2$—MeOH), and reprecipitated from a mixture of CH$_2$Cl$_2$ and n-hexane to obtain the title compound (153 mg, 81%).

HPLC:21.52 min

1H NMR (DMSO-d6) δ (ppm); 1.35 (s, 3H, Dmt-5-CH$_3$), 1.50 (s, 3H, Dmt-5-CH$_3$), 2.27 (s, 3H, benzylamine-CH$_3$), 2.6–2.8 (m, 2H, Apns-4-CH$_2$), 3.70 (s, 3H, Apns-OCH$_3$), 4.14 (dd, 1H, J=4.3 Hz, 15.1 Hz, benzylamine-CH$_2$), 4.2–4.5 (m, 4H, benzylamine-CH$_2$, Dmt-4-CH, Apns-2-CH, and Apns-3-CH), 4.98 (d, 1H, J=9.2 Hz, Dmt-2-CH$_2$), 5.12 (d, 1H, J=8.9 Hz, Dmt-2-CH$_2$), 5.3–5.5 (m, 3H, Apns-2-OH, benzoyl-NH$_2$), 6.37 (d, 1H, J=6.8 Hz, aromatic), 6.7–6.9 (m, 3H, aromatic), 6.98 (t, 1H, J=7.8 Hz, aromatic), 7.1–7.2 (br, 1H, aromatic), 7.2–7.4 (m, 3H, aromatic), 8.2–8.4 (m, 2H, Apns-NH, benzylamine-NH):

MS(TOF) m/z=626(M$^+$+H)

Example 5

(R)-N-(2-methylbenzyl)-3-[(2S,3S)-2-hydroxy-3-(3-hydroxy-2-methylbenzoyl)amino-4-(4-ethoxyphenyl)butanoyl]-5,5-dimethyl-1,3-thiazolidine-4-carboxamide The title compound was synthesized in the same manner as in Example 1 using (2S,3S)-3-tert-butoxycarbonylamino-2-hydroxy-4-(4-ethoxyphenyl)butanoic acid.

HPLC:19.31 min

1H NMR (DMSO-d6) δ (ppm); 1.29 (t, 3H, J=7.0 Hz, OEt-CH$_3$), 1.35 (s, 3H, Dmt-5-CH$_3$), 1.50 (s, 3H, Dmt-5-CH$_3$), 1.86 (s, 3H, benzoyl-CH$_3$), 2.26 (s, 3H, benzylamine-CH$_3$), 2.6–2.8 (m, 2H, Apns-4-CH$_2$), 3.96 (q, 2H, J=6.9 Hz, Apns-OCH$_2$), 4.14 (dd, 1H, J=4.3 Hz, 15.1 Hz, benzylamine-CH$_2$), 4.2–4.5 (m, 4H, benzylamine-CH$_2$, Dmt-4-CH, Apns-2-CH, and Apns-3-CH), 5.00 (d, 1H, J=9.5 Hz, Dmt-2-CH$_2$), 5.13 (d, 1H, J=9.2 Hz, Dmt-2-CH$_2$), 5.43 (d, 1H, J=7.0 Hz, Apns-2-OH), 6.57 (d, 1H, J=6.8 Hz, aromatic), 6.78 (d, 2H, J=8.6 Hz, aromatic), 6.96 (t, 1H, J=7.6 Hz, aromatic), 7.1–7.2 (m, 3H, aromatic), 7.22 (d, 2H, J=8.4 Hz, aromatic), 7.3–7.4 (m, 1H, aromatic), 8.09 (d, 1H, J=8.4 Hz, Apns-NH), 8.3 (br, 1H, benzylamine-NH), 9.39 (s, 1H, benzoyl-OH):

MS(TOF) m/z=621(M$^+$+H)

Example 6

(R)-N-(2-methylbenzyl)-3-[(2S,3S)-2-hydroxy-3-(3-hydroxy-2-methylbenzoyl)amino-4-(3,4-methylenedioxyphenyl)butanoyl]-5,5-dimethyl-1,3-thiazolidine-4-carboxamide The title compound was synthesized in the same manner as in Example 1 using (2S,3S)-3-tert-butoxycarbonylamino-2-hydroxy-4-(3,4-methylenedioxyphenyl)butanoic acid.

HPLC:18.84 min $^1$H NMR (DMSO-d6) δ (ppm); 1.35 (s, 3H, Dmt-5-CH$_3$), 1.50 (s, 3H, Dmt-5-CH$_3$), 1.87 (s, 3H, benzoyl-CH$_3$), 2.27 (s, 3H, benzylamine-CH$_3$), 2.6–2.8 (m, 2H, Apns-4-CH$_2$), 4.12 (dd, 1H, J=4.3 Hz, 15.1 Hz, benzylamine-CH$_2$), 4.3–4.6 (m, 4H, benzylamine-CH$_2$, Dmt-4-CH, Apns-2-CH, and Apns-3-CH), 5.00 (d, 1H, J=9.2 Hz, Dmt-2-CH$_2$), 5.15 (d, 1H, J=9.2 Hz, Dmt-2-CH$_2$), 5.37 (d, 1H, J=6.5 Hz, Apns-2-OH), 5.93 (s, 2H, Apns-O-CH$_2$—), 6.59 (d, 1H, J=7.6 Hz, aromatic), 6.7–6.9 (m, 3H, aromatic), 6.9–7.0 (m, 2H, aromatic), 7.1–7.2 (m, 3H, aromatic), 7.3–7.4 (m, 1H, aromatic), 8.14 (d, 1H, J=8.9 Hz, Apns-NH), 8.35 (t, 1H, J=5.4 Hz), 9.40 (s, 1H, benzoyl-OH):

MS (TOF) m/z=621 (M$^+$+H)

Example 7

(R)-N-(2-methylbenzyl)-3-[(2S,3S)-2-hydroxy-3-(3-hydroxy-2-methylbenzoyl)amino-4-(4-n-propoxyphenyl)butanoyl]-5,5-dimethyl-1,3-thiazolidine-4-carboxamide The title compound was synthesized in the same manner as in Example 1 using (2S,3S)-3-tert-butoxycarbonylamino-2-hydroxy-4-(4-n-propoxyphenyl)butanoic acid.

HPLC:20.94 min $^1$H NMR (DMSO-d6) δ (ppm); 0.96 (t, 3H, J=7.3 Hz, OnPr-CH$_3$), 1.35 (s, 3H, Dmt-5-CH$_3$), 1.50 (s, 3H, Dmt-5-CH$_3$), 1.66–1.73 (m, 2H, OCH$_2$—CH$_2$—CH$_3$), 1.86 (s, 3H, benzoyl-CH$_3$) 2.26 (s, 3H, benzylamine-CH$_3$), 2.6–2.8 (m, 2H, Apns-4-CH$_2$) 3.87 (t, 2H, J=6.3 Hz, Apns-OCH$_2$), 4.14 (dd, 1H, J=4.3 Hz, 15.1 Hz, benzylamine-CH$_2$), 4.3–4.5 (m, 4H, benzylamine-CH$_2$, Dmt-4-CH, Apns-2-CH, and Apns-3-CH), 5.00 (d, 1H, J=8.9 Hz, Dmt-2-CH$_2$), 5.13 (d, 1H, J=9.2 Hz, Dmt-2-CH$_2$), 5.44 (d, 1H, J=7.0 Hz, Apns-2-OH), 6.58 (d, 1H, J=7.6 Hz, aromatic), 6.7–6.8 (m, 3H, aromatic), 6.96 (t, 1H, J=7.8 Hz, aromatic), 7.1–7.2 (br, 3H, aromatic), 7.26 (d, 2H, J=8.9 Hz, aromatic), 7.25–7.35 (m, 1H, aromatic), 8.09 (d, 1H, J=8.4 Hz, Apns-NH), 8.31 (br, 1H, benzylamine-NH), 9.39 (s, 1H, benzoyl-OH)

MS (TOF) m/z=635 (M$^+$+H)

Example 8

(R)-N-(2-methylbenzyl)-3-[(2S,3S)-2-hydroxy-3-(3-hydroxy-2-methylbenzoyl)amino-4-(4-isopropoxyphenyl)butanoyl]-5,5-dimethyl-1,3-thiazolidine-4-carboxamide The title compound was synthesized in the same manner as in Example 1 using (2S,3S)-3-tert-butoxycarbonylamino-2-hydroxy-4-(4-isopropoxyphenyl)butanoic acid.

HPLC:20.28 min $^1$H NMR (DMSO-d6) d (ppm); 1.22 (s, 3H, iPr-CH$_3$), 1.24 (s, 3H, iPr-CH$_3$), 1.35 (s, 3H, Dmt-5-CH$_3$), 1.50 (s, 3H, Dmt-5-CH$_3$), 1.84 (s, 3H, benzoyl- CH$_3$), 2.26 (s, 3H, benzylamine-CH$_3$), 2.6–2.8 (m, 2H, Apns-4-CH$_2$), 4.14 (dd, 1H, J=4.3 Hz, 15.1 Hz, benzylamine-CH$_2$), 4.3–4.6 (m, 5H, benzylamine-CH$_2$, Dmt-4-CH, Apns-2-CH, Apns-OCH, and Apns-3-CH), 5.01 (d, 1H, J=8.9 Hz, Dmt-2-CH$_2$), 5.14 (d, 1H, J=9.2 Hz, Dmt-2-CH$_2$) 5.44 (d, 1H, J=6.8 Hz, Apns-2-OH), 6.57 (d, 1H, J=7.6 Hz, aromatic), 6.75–6.79 (m, 3H, aromatic), 6.95 (t, 1H, J=7.8 Hz), 7.10–7.14 (m, 3H, aromatic), 7.20 (d, 2H, J=8.1 Hz, aromatic), 7.28–7.31 (m, 1H, aromatic), 8.09 (d, 1H, J=8.4 Hz, Apns-NH), 8.31 (bt, 1H, benzylamine-NH), 9.34 (s, 1H, benzoyl-OH):
MS (TOF) m/z=635 (M$^+$+H)

Example 9
(R)-N-(2-methylbenzyl)-3-[(2S,3S)-2-hydroxy-3-(3-hydroxy-2-methylbenzoyl)amino-4-(4-metylphenyl)butanoyl]-5,5-dimethyl-1,3-thiazolidine-4-carboxamide The title compound was synthesized in the same manner as in Example 1 using (2S,3S)-3-tert-butoxycarbonylamino-2-hydroxy-4-(4-methylphenyl)butanoic acid.
HPLC 19.98 min
$^1$H NMR (DMSO-d6) δ (ppm); 1.35 (s, 3H, Dmt-5-CH$_3$), 1.50 (s, 3H, Dmt-5-CH$_3$), 1.86 (s, 3H, benzoyl-CH$_3$), 2.25 (s, 3H, Apns-CH$_3$), 2.26 (s, 3H, benzylamine-CH$_3$), 2.6–2.9 (m, 2H, Apns-4-CH$_2$), 4.14 (dd, 1H, J=4.3 Hz, 15.1 Hz, benzylamine-CH$_2$), 4.3–4.5 (m, 4H, benzylamine-CH$_2$, Dmt-4-CH, Apns-2-CH, and Apns-3-CH), 5.00 (d, 1H, J=9.5 Hz, Dmt-2-CH$_2$), 5.12 (d, 1H, J=9.2 Hz, Dmt-2-CH$_2$), 5.47 (d, 1H, J=6.2 Hz, Apns-2-OH), 6.57 (d, 1H, J=7.3 Hz, aromatic), 6.78 (d, 1H, J=7.8 Hz, aromatic), 6.96 (t, 1H, J=7.8 Hz), 7.0–7.2 (m, 5H, aromatic), 7.20 (d, 2H, J=7.6 Hz, aromatic), 7.28–7.31 (m, 1H, aromatic), 8.08 (d, 1H, J=7.8 Hz, Apns-NH), 8.30 (br, 1H, benzylamine-NH), 9.39 (s, 1H, benzoyl-OH):
MS (TOF) m/z=591 (M$^+$+H)

Example 10
(R)-N-(2-methylbenzyl)-3-[(2S,3S)-2-hydroxy-3-(3-hydroxy-2-methylbenzoyl)amino-4-(4-isopropylphenyl)butanoyl]-5,5-dimethyl-1,3-thiazolidine-4-carboxamide The title compound was synthesized in the same manner as in Example 1 using (2S,3S)-3-tert-butoxycarbonylamino-2-hydroxy-4-(4-isopropylphenyl)butanoic acid.
HPLC:21.59 min
$^1$H NMR (DMSO-d6) δ (ppm); 1.17 (d, 6H, J=6.8 Hz, iPr-CH$_3$), 1.35 (s, 3H, Dmt-5-CH$_3$), 1.49 (s, 3H, Dmt-5-CH$_3$), 1.78 (s, 3H, benzoyl-CH$_3$), 2.26 (s, 3H, benzylamine-CH$_3$), 2.6–2.9 (m, 3H, Apns-4-CH$_2$, iPr-CH), 4.10 (dd, 1H, J=4.3 Hz, 15.1 Hz, benzylamine-CH$_2$), 4.3–4.5 (m, 4H, benzylamine-CH$_2$, Dmt-4-CH, Apns-2-CH, and Apns-3-CH), 5.01 (d, 1H, J=9.2 Hz, Dmt-2-CH$_2$), 5.14 (d, 1H, J=9.5 Hz, Dmt-2-CH$_2$), 5.48 (d, 1H, J=6.5 Hz, Apns-2-OH), 6.55 (d, 1H, J=7.3 Hz, aromatic), 6.77 (d, 1H, J=7.8 Hz, aromatic), 6.94 (t, 1H, J=7.6 Hz, aromatic), 7.05–7.15 (m, 5H, aromatic), 7.22 (d, 2H, J=7.8 Hz, aromatic), 7.28–7.31 (m, 1H, aromatic), 8.08 (d, 1H, J=7.6 Hz, Apns-NH), 8.30 (t, 1H, J=5.7 Hz, benzylamine-NH), 9.37 (s, 1H, benzoyl-OH):
MS (TOF) m/z=619 (M$^+$+H)

Example 11
(R)-N-(2-methylbenzyl)-3-[(2S,3S)-2-hydroxy-3-(3-hydroxy-2-methylbenzoyl)amino-4-(4-chlorophenyl)butanoyl]-5,5-dimethyl-1,3-thiazolidine-4-carboxamide The title compound was synthesized in the same manner as in Example 1 using (2S,3S)-3-tert-butoxycarbonylamino-2-hydroxy-4-(4-chlorophenyl)butanoic acid.
HPLC:20.22 min
$^1$H NMR (DMSO-d6) δ (ppm); 1.35 (s, 3H, Dmt-5-CH$_3$), 1.50 (s, 3H, Dmt-5-CH$_3$), 1.82 (s, 3H, benzoyl-CH$_3$), 2.26 (s, 3H, benzylamine-CH$_3$), 2.7–2.9 (m, 2H, Apns-4-CH$_2$), 4.14 (dd, 1H, J=4.3 Hz; 15.1 Hz, benzylamine-CH$_2$), 4.3–4.5 (m, 4H, benzylamine-CH$_2$, Dmt-4-CH, Apns-2-CH, and Apns-3-CH), 5.00 (d, 1H, J=9.5 Hz, Dmt-2-CH$_2$), 5.15 (d, 1H, J=9.2 Hz, Dmt-2-CH$_2$), 5.47 (d, 1H, J=6.5 Hz, Apns-2-OH), 6.57 (d, 1H, J=7.3 Hz, aromatic), 6.78 (d, 1H, J=7.8 Hz, aromatic), 6.96 (t, 1H, J=7.8 Hz, aromatic), 7.0–7.2 (m, 3H, aromatic), 7.2–7.4 (m, 5H, aromatic), 8.17 (d, 1H, J=8.6 Hz, Apns-NH), 8.34 (bt, 1H, benzylamine-NH), 9.40 (s, 1H, benzoyl-OH):
MS (TOF) m/z=611 (M$^{30}$+H)

Example 12
(R)-N-(2-methylbenzyl)-3-[(2S,3S)-2-hydroxy-3-(3-amino-2-chlorobenzoyl)amino-4-(4-ethoxyphenyl)butanoyl]-5,5-dimethyl-1,3-thiazolidine-4-carboxamide The title compound was synthesized in the same manner as in Example 4 using (2S,3S)-3-tert-butoxycarbonylamino-2-hydroxy-4-(4-ethoxyphenyl)butanoic acid.
HPLC:21.33 min
$^1$H NMR (DMSO-d6) δ (ppm); 1.29 (t, 3H, J=7.0 Hz, OEt-CH$_3$), 1.35 (s, 3H, Dmt-5-CH$_3$), 1.50 (s, 3H, Dmt-5-CH$_3$), 2.27 (s, 3H, benzylamine-CH$_3$), 2.6–2.8 (m, 2H, Apns-4-CH$_2$), 3.96 (q, 2H, J=6.8 Hz, Apns-OCH$_2$), 4.14 (dd, 1H, J=4.3 Hz, 15.1 Hz, benzylamine-CH$_2$), 4.2–4.5 (m, 4H, benzylamine-CH$_2$, Dmt-4-CH, Apns-2-CH, and Apns-3-CH), 4.98 (d, 1H, J=9.2 Hz, Dmt-2-CH$_2$) 5.12 (d, 1H, J=9.5 Hz, Dmt-2-CH$_2$), 5.3–5.5 (m, 3H, Apns-2-OH, benzoyl-NH$_2$), 6.36 (d, 1H, J=6.2 Hz, aromatic), 6.7–6.9 (m, 3H, aromatic), 6.98 (t, 1H, J=7.8 Hz, aromatic), 7.1–7.2 (br, 3H, aromatic), 7.23 (d, 2H, J=8.9 Hz, aromatic), 7.3–7.4 (m, 1H, aromatic), 8.28–8.34 (m, 2H, Apns-NH, benzylamine-NH):
MS (TOF) m/z=640 (M$^+$+H)

Example 13
(R)-N-(2-methylbenzyl)-3-[(2S,3S)-2-hydroxy-3-(3-amino-2-chlorobenzoyl)amino-4-(3,4-methylenedioxyphenyl)butanoyl]-5,5-dimethyl-1,3-thiazolidine-4-carboxamide The title compound was synthesized in the same manner as in Example 4 using (2S,3S)-3-tert-butoxycarbonylamino-2-hydroxy-4-(3,4-methylenedioxyphenyl)butanoic acid.
HPLC: 19.13 min
$^1$H NMR (DMSO-d6) δ (ppm); 1.36 (s, 3H, Dmt-5-CH$_3$), 1.51 (S, 3H, Dmt-5-CH$_3$), 2.27 (s, 3H, benzylamine-CH$_3$), 2.6–2.8 (m, 2H, Apns-4-CH$_2$), 4.14 (dd, 1H, J=4.3 Hz, 15.1 Hz, benzylamine-CH$_2$), 4.2–4.5 (m, 4H, benzylamine-CH$_2$, Dmt-4-CH, Apns-2-CH, and Apns-3-CH), 4.98 (d, 1H, J=8.6 Hz, Dmt-2-CH$_2$), 5.14 (d, 1H, J=8.9 Hz, Dmt-2-CH$_2$), 5.32 (d, 1H, J=6.8 Hz, Apns-2-OH), 5.42 (s, 2H, benzoyl-NH$_2$), 5.93 (s, 2H, Apns-O-CH$_2$—), 6.38 (d, 1H, J=7.6 Hz, aromatic), 6.7–6.8 (m, 3H, aromatic), 6.9–7.0 (m, 2H, aromatic), 7.1–7.2 (m, 4H, aromatic), 7.3–7.4 (m, 2H, aromatic), 8.3–8.4 (m, 2H, Apns-NH, benzylamine-NH):
MS (TOF) m/z=640 (M$^+$+H)

Example 14
(R)-N-(2,6-dimethylbenzyl)-3-[(2S,3S)-2-hydroxy-3-(3-amino-2-chlorobenzoyl)amino-4-(4-methoxyphenyl)butanoyl]-5,5-dimethyl-1,3-thiazolidine-4-carboxamide
Step 1
(R)-N-(2,6-dimethylbenzyl)-5,5-dimethyl-1,3-thiazolidine-4-carboxamide DPP-Cl (114 μl) was added to a solution of Boc-Dmt-OH (131 mg) and TEA (83 μl) in EtOAc (2 ml) while cooling with ice, and the mixture was stirred for one hour. After the addition of 2,6-dimethylbenzylamine-HCl (86 mg) and TEA (167 μl), the mixture was stirred overnight. The reaction mixture was washed with 5% Na$_2$CO$_3$ (×2), 1N HCl, and 5% NaCl, and dried over MgSO$_4$. After filtration and concentration, 4N HCl/EtOAc (2 ml) was added. The solution was stirred for three hours and neutralized with 2N NaOH while cooling with ice. The organic layer was washed with 5% NaCl, dried over MgSO$_4$, filtered and concentrated. The residue was recrystallized from n-hexane to obtain the title compound (70 mg, 50%).
$^1$H NMR (DMSO-d6) δ (ppm); 1.15 (s, 3H), 1.45 (s, 3H), 2.32 (s, 6H), 3.23 (s, 1H), 3.69 (br, 1H), 3.99 (d, 1H, J=8.9 Hz), 4.20–4.39 (m, 3H), 7.01–7.13 (m, 3H), 7.99 (br, 1H);

Step 2
(R)-N-(2,6-methylbenzyl)-3-[(2S,3S)-3-amino-2-hydroxy-4-(4-methoxyphenyl)butanoyl]-5,5-dimethyl-1,3-thiazolidine-4-carboxamide Boc-Apns (4-OMe)-OH (163 mg), HOBt (68 mg), and DCC (113 mg) were added to a solution of (R)-N-(2,6-dimethylbenzyl)-5,5-dimethyl-1,3-thiazolidine-4-carboxamide (153 mg) in EtOAc (5 ml), and the mixture was stirred overnight. The reaction mixture was filtered and washed with 5% $Na_2CO_3$ (×2), 1N HCl, and 5% NaCl, dried over $MgSO_4$, filtered and concentrated. Then, 4N HCl/EtOAc (10 ml) was added and the mixture was stirred for one hour. The reaction mixture was concentrated, dissolved in water, filtered, and adjusted to pH 10 by the addition of 3N NaOH, followed by crystallization and filtration. The crystals were dried, and recrystallized from EtOAc to obtain the title compound (129 mg, 53%). H NMR (DMSO-d6) δ (ppm); 0.6–0.8 (br, 2H), 1.34 (s, 3H), 1.52 (s, 3H), 2.09 (s, 6H), 2.0–2.1 (m, 1H), 2.3–2.5 (m, 1H), 3.02 (d, 1H, J=11.3 Hz), 3.79 (s, 3H), 3.95–4.01 (br, 1H), 4.10 (br, 2H), 4.27 (s, 1H), 4.84 (s, 2H), 5.22 (d, 1H, J=8.1 Hz), 6.66–6.77 (m, 3H), 6.90 (d, 2H, J=8.6 Hz), 6.99 (d, 2H, J=8.4 Hz), 8.17 (br, 1H);

Step 3
(R)-N-(2,6-dimethylbenzyl)-3-[(2S,3S)-2-hydroxy-3-(3-amino-2-chlorobenzoyl)amino-4-(4-methoxyphenyl)butanoyl]-5,5-dimethyl-1,3-thiazolidine-4-carboxamide EDC.HCl (42 mg) was added to a solution of the compound obtained in Step 2 of Example 14 (94 mg), 3-amino-2-chlorobenzoic acid (35 mg), and HOBt (27 mg) in DMF (2 ml), and the mixture was stirred overnight. The reaction mixture was extracted with EtOAc and $H_2O$. The extract was washed with 5% $Na_2CO_3$ (×2), 1N HCl, and 5% NaCl, dried over $MgSO_4$, filtered and concentrated, and the residue was purified by silica gel column chromatography ($CH_2Cl_2$—MeOH) and reprecipitated from a mixture of $CH_2Cl_2$ and n-hexane to obtain the title compound (77 mg, 62%).
HPLC: 21.00 min
$^1$H NMR (DMSO-d6) δ (ppm); 1.36 (s, 3H, Dmt-5-$CH_3$), 1.46 (s, 3H, Dmt-5-$CH_3$), 2.32 (s, 6H, benzylamine-$CH_3$), 2.6–2.7 (m, 2H, Apns-4-$CH_2$), 3.72 (s, 3H, Apns-O$CH_3$), 4.1–4.3 (m, 2H, benzylamine-$CH_2$, and Apns-3-CH), 4.44–4.54 (m, 3H, benzylamine-$CH_2$, Dmt-4-CH, and Apns-2-CH), 4.96 (d, 1H, J=9.5 Hz, Dmt-2-$CH_2$), 5.15 (d, 1H, J=8.9 Hz, Dmt-2-$CH_2$) 5.21 (d, 1H, J=6.8 Hz, Apns-2-OH), 5.40 (s, 2H, benzoyl-$NH_2$), 6.38 (d, 1H, J=7.3 Hz, aromatic), 6.7–6.9 (m, 3H, aromatic), 6.9–7.1 (m, 4H, aromatic), 7.31 (d, 2H, J=8.4 Hz, aromatic), 8.10 (m, 1H, benzylamine-NH), 8.39 (d, 1H, J=8.4 Hz, Apns-NH):
MS (TOF) m/z=640 ($M^+$+H)

Example 15
(R)-N-(2,6-dimethylbenzyl)-3-[(2S,3S)-2-hydroxy-3-(3-amino-2-chlorobenzoyl) amino-4-(3,4-methylenedioxyphenyl) butanoyl]-5, 5-dimethyl-1,3-thiazolidine-4-carboxamide The title compound was synthesized in the same manner as in Example 14 using (2S,3S)-3-tert-butoxycarbonylamino-2-hydroxy-4-(3,4-methylenedioxyphenyl) butanoic acid.
HPLC:19.96 min.
$^1$H NMR (DMSO-d6) δ (ppm); 1.36 (s, 3H, Dmt-5-$CH_3$), 1.46 (s, 3H, Dmt-5-$CH_3$),2.32 (s, 6H, benzylamine-$CH_{3×2}$), 2.6–2.7 (m, 2H, Apns-4-CH), 4.1–4.3 (m, 2H, benzylamine-$CH_2$, Apns-3-CH), 4.44–4.54 (m, 3H, benzylamine-$CH_2$, Dmt-4-CH, and Apns-2-CH), 4.95 (d, 1H, J=8.6 Hz, Dmt-2-$CH_2$), 5.15–5.19 (m, 2H, Dmt-2-$CH_2$, Apns-2-OH), 5.41 (s, 2H, benzoyl-$NH_2$), 5.94 (s, 2H, O—$CH_2$—O), 6.37–6.40 (m, 1H, aromatic), 6.76–6.87 (m, 3H, aromatic), 6.96–7.09 (m, 5H, aromatic), 8.12 (br, 1H, benzylamine-NH), 8.42 (d, 1H, J=8.4 Hz, Apns-NH):
MS (TOF) m/z=654 ($M^+$+H)

Example 16

(S107–159)
(R)-N-(2-methylbenzyl)-3-[(2S,3S)-2-hydroxy-3-(3-amino-2-chlorobenzoyl)amino-4-(3-methoxyphenyl)butanoyl]-5,5-dimethyl-1,3-thiazolidine-4-carboxamide The title compound was synthesized in the same manner as in Example 4 using (2S,3S)-3-tert-butoxycarbonylamino-2-hydroxy-4-(3-methoxyphenyl)butanoic acid.
HPLC: 19.59min
$^1$H NMR (DMSO-d6) δ (ppm); 1.36 (s, 3H, Dmt-5-$CH_3$), 1.51 (s, 3H, Dmt-5-$CH_3$), 2.27 (s, 3H, benzylamine-$CH_3$), 2.7–2.8 (m, 2H, Apns-4-$CH_2$), 3.67 (s, 3H, Apns-O $CH_3$), 4.14 (dd, 1H, J=4.3 Hz, 15.1 Hz, benzylamine-$CH_2$),4.2–4.5 (m, 4H, benzylamine-$CH_2$, Dmt-4-CH, Apns-2-CH, and Apns-3-CH), 4.99 (d, 1H, J=9.2 Hz, Dmt-2-$CH_2$), 5.14 (d, 1H, J=8.9 Hz, Dmt-2-$CH_2$), 5.35 (d, 1H, J=7.0 Hz, Apns-2-OH), 5.41 (s, 2H, benzoyl-$NH_2$), 6.35–6.37 (m, 1H, aromatic), 6.6–6.8 (m, 2H, aromatic), 6.9–7.0 (m, 3H, aromatic), 7.1–7.2 (m, 4H, aromatic), 7.3–7.4 (m, 1H, aromatic), 8.3–8.4 (m, 2H, Apns-NH, benzylamine-NH):
MS (TOF) m/z=626 ($M^+$+H)

Example 17
(R)-N-tert-Butyl-3-[(2S,3S)-2-hydroxy-3-(3-hydroxy-2-methylbenzoyl)amino-4-(4-methoxyphenyl)butanoyl]-5,5-dimethyl-1,3-thiazolidine-4-carboxamide
Step 1
(R)-N-tert-Butyl-5,5-dimethyl-1,3-thiazolidine-4-carboxamide DPP-Cl (4.55 ml) was added to a solution of Boc-Dmt-OH (5.22 g) and TEA (3.34 ml) in EtOAc (100 ml) while cooling with ice, and the mixture was stirred for one hour. After the addition of tert-butylamine (6.30 ml), the mixture was stirred overnight. The reaction mixture was washed with 1N HCl, 3% $K_2CO_3$, and brine, and dried over $MgSO_4$. The residue was dissolved in $CH_2Cl_2$ (30 ml) and 4N HCl/dioxane (30 ml) was added. The resulting solution was stirred for two hours and concentrated. The residue was dissolved in water to remove insoluble component by filtration. The filtrate was washed with $CH_2Cl_2$, adjusted to pH 8 with the addition of $K_2CO_3$, and extracted with $CH_2Cl_2$. The extract was dried and concentrated. The title compound (3.01 g, 70%) was obtained by recrystallizing from n-hexane.
$^1$H NMR (DMSO-d6) δ (ppm): 1.16 (s, 3H), 1.27 (s, 9H), 1.52 (s, 3H), 3.16 (d, 1H, J=13.2 Hz), 3.46–3.58 (m, 1H), 3.99 (dd, 1H, J=11.8 Hz, 9.2 Hz), 4.26 (dd, 1H, J=7.3 Hz, 9.2 Hz), 7.47 (s, 1H);
Step 2
(R)-N-tert-Butyl-3-[(2S,3S)-3-amino-2-hydroxy-4-(4-methoxyphenyl)butanoyl]-5,5-dimethyl-1,3-thiazolidine-4-carboxamide Boc-Apns (4-OMe)-OH (260 mg), HOBt (108 mg), and DCC (181 mg) were added to a solution of the compound obtained in Step 1 (173 mg) in EtOAc (10 ml), and the mixture was stirred overnight. The reaction mixture was filtered and washed with 5% $Na_2CO_3$ (×2), 1N HCl, and 5% NaCl, dried over $MgSO_4$, filtered and concentrated. Then, 4N HCl /EtOAc (10 ml) was added and the mixture was stirred for one hour. The reaction mixture was concentrated, dissolved in water, filtered, and adjusted to pH 10 by the addition of 3N NaOH, followed by extraction with EtOAc.

The extract was washed with 5% NaCl, dried over MgSO$_4$, filtered and concentrated. The residue was recrystallized from n-hexane to obtain the title compound (202 mg, 60%).
$^1$H NMR (DMSO-d6) δ (ppm);1.21 (s, 9H), 1.35 (s, 3H), 1.3–1.6 (m, 2H), 1.49 (s, 3H), 2.26–2.34 (m, 1H), 2.81–2.95 (m, 2H), 4.08 (br, 1H), 4.36 (s, 1H), 4.88 (s, 2H), 6.85 (d, 2H, J=8.1 Hz), 7.16 (d, 1H, J=8.1 Hz), 7.53 (s, 1H):

Step 3
(R)-N-tert-Butyl-3-[(2S,3S)-2-hydroxy-3-(3-hydroxy-2-methylbenzoyl)amino-4-(4-methoxyphenyl)butanoyl]-5,5-dimethyl-1,3-thiazolidine-4-carboxamide DPP-Cl (43 μl) and TEA (31 μl) were added to a solution of 3-acetoxy-2-methylbenzoic acid (41 mg) in EtOAc (2 ml), and the mixture was stirred for one hour. After the addition of the compound obtained in Step 2 (85 mg) and TEA (34 μl), the mixture was stirred overnight. The reaction mixture was washed with 5% Na$_2$CO$_3$ (×2), 1N HCl, and 5% NaCl. After concentration, MeOH (1.5 ml) and 1N NaOH (300 μl) were added. After stirring for one hour, 1N HCl was added to make the reaction mixture acidic. The resulting mixture was extracted with EtOAc. The extract was washed with 5% Na$_2$CO$_3$ (×2), 1N HCl, and 5% NaCl, dried over MgSO$_4$, filtered and concentrated. The residue was recrystallized from a mixture of EtOAc and n-hexane to obtain the title compound (90 mg, 81%).
HPLC: 18.26 min
$^1$H NMR (DMSO-d6) δ (ppm); 1.27 (s, 9H, tBu), 1.40 (s, 3H, Dmt-5-CH$_3$), 1.49 (s, 3H, Dmt-5-CH$_3$), 1.84 (s, 3H, benzoyl-CH$_3$), 2.6–2.8 (m, 2H, Apns-4-CH$_2$), 3.71 (s, 3H, Apns-OCH$_3$) 4.2–4.3 (m, 1H, Apns-3-CH), 4.49–4.52 (br, 2H, Dmt-4-CH, Apns-2-CH), 4.97 (d, 1H, J=8.9 Hz, Dmt-2-CH$_2$), 5.14 (d, 1H, J=8.9 Hz, Dmt-2-CH$_2$), 5.23 (d, 1H, J=7.3 Hz, Apns-2-OH), 6.57 (d, 1H, J=7.3 Hz, aromatic), 6.7–6.8 (m, 3H, aromatic), 6.96 (t, 1H, J=7.6 Hz, aromatic), 7.29 (d, 2H, J=8.4 Hz, aromatic), 7.63 (s, 1H, tBu-NH), 8.18 (d, 1H, J=8.4 Hz, Apns-NH), 9.38 (s, 1H, benzoyl-OH):
MS (TOF) m/z=559 (M$^+$+H)

Example 18
(R)-N-tert-Butyl-3-[(2S,3S)-2-hydroxy-3-(2,6-dimethylphenoxyacetyl)amino-4-(4-methoxyphenyl)butanoyl]-5,5-dimethyl-1,3-thiazolidine-4-carboxamide EDC-HCl (63 mg) was added to a solution of the compound obtained in Step 2 of Example 17 (127 mg), 2,6-dimethylphenoxyacetic acid (54 mg), and HOBt (41 mg) in DMF, and the mixture was stirred overnight. The reaction mixture was diluted with ethyl acetate, washed with 5% Na$_2$CO$_3$ (×2), 1N HCl, and 5% NaCl, dried over MgSO$_4$, filtered and concentrated. The residue was purified by silica gel column chromatography and recrystallized from a mixture of EtOAc and n-hexane to obtain the title compound (130 mg).
HPLC:21.71 min
$^1$H NMR (DMSO-d6) δ (ppm); 1.27 (s, 9H, tBu), 1.40 (s, 3H, Dmt-5-CH$_3$), 1.49 (s, 3H, Dmt-5-CH$_3$), 2.16 (s, 6H, benzyl-CH$_3$), 2.6–2.8 (m, 2H, Apns-4-CH$_2$), 3.71 (s, 3H, Apns-OCH$_3$) 4.00 (d, 1H, J=14.3 Hz, PhOCH$_2$—), 4.06–4.29 (m, 2H, PhOCH$_2$—, Apns-3-CH), 4.46–4.52 (m, 2H, Dmt-4-CH, Apns-2-CH), 4.95 (m, 2H, Dmt-2-CH$_2$), 5.33 (d, 1H, J=6.8 Hz, Apns-2-OH), 6.78–6.83 (m, 2H, aromatic), 6.90–7.03 (m, 3H, aromatic), 7.28 (d, 2H, J=8.4 Hz, aromatic), 7.67 (s, 1H, tBu-NH), 8.11 (d, 1H, J=8.9 Hz, Apns-NH):
MS (TOF) m/z=587 (M$^+$+H)

Example 19
(R)-N-(2,6-dichlorolbenzyl)-3-[(2S,3S)-2-hydroxy-3-(3-amino-2-chlorobenzoyl)amino-4-(4-methoxyphenyl)butanoyl]-5,5-dimethyl-1,3-thiazolidine-4-carboxamide The title compound was synthesized in the same manner as in Example 4 using 2,6-dichlorobenzylamine instead of 2-methylbenzylamine.
HPLC: 20.94 min
$^1$H NMR (DMSO-d6) δ (ppm); 1.35 (s, 3H, Dmt-5-CH$_3$), 1.46 (s, 3H, Dmt-5-CH$_3$), 2.6–2.7 (m, 2H, Apns-4-CH$_2$), 3.72 (s, 3H, Apns-OCH$_3$), 4.15–4.30 (br, 1H, benzylamine-CH$_2$), 4.47–4.64 (m, 4H, benzylamine-CH$_2$, Dmt-4-CH, Apns-2-CH, and Apns-3-CH), 4.98 (d, 1H, J=8.9 Hz, Dmt-2-CH$_2$), 5.11 (d, 1H, J=9.5 Hz, Dmt-2-CH$_2$), 5.23 (d, 1H, J=6.8 Hz, Apns-2-OH), 5.4 (br, 2H, benzoyl-NH$_2$), 6.37 (d, 1H, J=6.2 Hz, aromatic), 6.7–6.9 (m, 3H, aromatic), 6.99 (t, 1H, J=7.8 Hz, aromatic), 7.28–7.39 (m, 3H, aromatic), 7.45–7.51 (m, 2H, aromatic), 8.32 (br, 1H, benzylamine-NH), 8.39 (d, 1H, J=8.4 Hz, Apns-NH,):
MS (TOF) m/z=681 (M$^+$+H)

Example 20
(R)-N-((S)-1-indanyl)-3-[(2S,3S)-2-hydroxy-3-(3-amino-2-chlorobenzoyl)amino-4-(4-methoxyphenyl)butanoyl]3-5,5-dimethyl-1,3-thiazolidine-4-carboxamide The title compound was synthesized in the same manner as in Example 4 using S-1-aminoindan instead of 2-methylbenzylamine.
HPLC:19.96 min
$_1$H NMR (DMSO-d6) δ (ppm); 1.46 (s, 3H), 1.51 (s, 3H), 1.8–1.9 (m, 1H), 2.3–2.4 (m, 1H), 2.6–3.0 (m, 4H), 3.71 (s, 3H), 4.2–4.3 (m, 1H), 4.45–4.55 (m, 2H), 5.01 (d, 1H, J=9.5 Hz), 5.13 (d, 1H, J=9.2 Hz), 5.28–5.42 (m, 4H), 6.37 (d, 1H, J=6.5 Hz), 6.77–6.80 (m, 3H), 6.99 (t, 1H, J=7.6 Hz), 7.17–7.26 (m, 6H), 8.43–8.40 (m, 3H):
MS (TOF) m/z=638 (M$^+$+H)

Example 21
(R)-N-(2-methylbenzyl)-3-[(2S,3S)-2-hydroxy-3-(3-amino-2-methylbenzoyl)amino-4-(4-methoxyphenyl)butanoyl]-5,5-dimethyl-1,3-thiazolidine-4-carboxamide EDC.HCl (42 mg) was added to a solution of the compound obtained in Step 2 of Example 1 (94 mg), 3-amino-2-methylbenzoic acid (30 mg), and HOBt (27 mg) in DMF while cooling with ice, and the mixture was stirred overnight. EtOAc was added and the mixture was washed with 5% Na$_2$CO$_3$ (×2) and 5% NaCl, dried over MgSO$_4$, filtered and concentrated. The residue was purified by silica gel column chromatography (CH$_2$Cl$_2$—MeOH) and reprecipitated from a mixture of CH$_2$Cl$_2$ and n-hexane to obtain the title compound (77 mg, 64%).
HPLC: 16.35 min
$^1$H NMR (DMSO-d6) δ (ppm); 1.35 (s, 3H, Dmt-5-CH$_3$), 1.50 (s, 3H, Dmt-5-CH$_3$), 1.76 (s, 3H, benzoyl-CH$_3$), 2.27 (s, 3H, benzylamine-CH$_3$), 2.6–2.8 (m, 2H, Apns-4-CH$_2$), 3.70 (s, 3H, Apns-4-OCH$_3$), 4.10 (dd, 1H, J=4.9 Hz, 15.1 Hz, benzylamine-CH$_2$), 4.2–4.5 (m, 4H, benzylamine-CH$_2$, Dmt-4-CH, Apns-2-CH, and Apns-3-CH), 5.01 (d, 1H, J=9.2 Hz, Dmt-2-CH$_2$), 5.13 (d, 1H, J=9.2 Hz, Dmt-2-CH$_2$), 4.9–5.2 (br, 2H, benzoyl-NH$_2$), 5.4 (br, 1H, Apns-2-OH), 6.37 (d, 1H, J=7.3 Hz, aromatic), 6.63 (d, 1H, J=8.4 Hz, aromatic), 6.78–6.89 (m, 3H, aromatic), 7.1–7,2 (m, 3H, aromatic), 7.24 (d, 2H, J=8.9 Hz, aromatic), 7.29–7.31 (m, 1H, aromatic), 8.04 (d, 1H, J=8.4 Hz, Apns-NH), 8.32 (t, 1H, J=5.3 Hz, benzylamine-NH):
MS (TOF) m/z=606 (M$^+$+H)

Synthesis of compounds of Reference Examples 1–4

These compounds were obtained by the synthesis in the same manner as in Examples 1–4, using Boc-Apns-OH instead of Boc-Apns-(4-OMe)-OH (see T. Mimoto et al., J. Med. Chem., 42, 1789–1802, 1999).

Test Example 1

Measurement of HIV protease inhibitory activity

The protease inhibitory activity was measured according to the method reported by T. Mimoto et al., J. Med. Chem., 42, 1789–1802 (1999) by using a recombinant HIV-1 protease (see Biochemistry, 250, 9, 264 (1990)) and a synthesized peptide substrate (H-Ser-Gln-Asn-Tyr-Pro-Ile-Val-OH). Specifically, reaction solutions (15 μl each) containing any one of the compounds synthesized in the above Examples 1–15 and Reference Examples 1–4, an inhibitor in which a known anti-AIDS agent (nelfinavir) is dissolved in DMSO in different concentrations, 10.5 nM HIV-1 protease, 20 mM synthesized peptide substrate, and 100 mM MES buffer solution (pH 6.5) were incubated at 37° C. for 60 minutes. Peptide fragments produced by cleaving the Tyr-Pro bonds in the synthesized peptide substrate was quantitatively measured by reverse phase HPLC. The protease inhibitory activity of each compound was indicated by the inhibitory rate assuming the enzyme activity of a DMSO control which does not contain the compound as 100%. Results of the inhibitory activity measurement are shown in Table 1.

Test Example 2

Measurement of anti-HIV activity

The anti-HIV activity of the compounds synthesized Examples 1–15 and Reference Examples 1–4 was measured according to the method reported by 0. S. Weislow et al. (J. Natl. Cancer Inst. 81, 577–586, 1989) using CEM-SS cells as host cells and HIV virus (HIV-1 IIIB strain)(see T. Mimoto et al., J. Med. Chem., 42, 1789–1802, 1999, etc.).

Specifically, the compounds synthesized Examples 1–15 and Reference Examples 1–5 in various concentrations were added to a culture medium on 96-well microtiter plates. Human blood serum was added to a final concentration of 50%, then HIV infected CEM-SS cells was added, followed by incubation in a CO2 atmosphere at 37° C. for 6 days. The cytopathic effect induced by HIV-1 IIIB was measured by tetrazolium dye XTT dyeing method to evaluate the 50% inhibitory concentration (IC50). The evaluation results are shown in Table 1.

TABLE 1

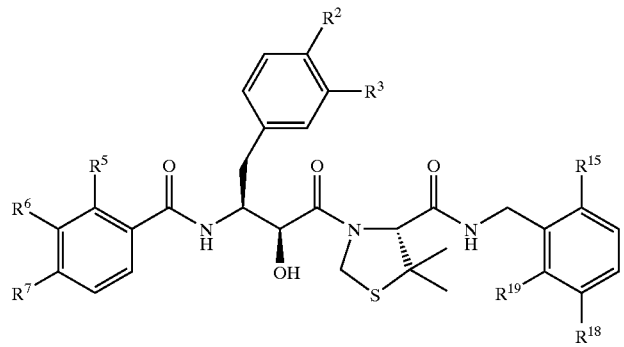

| Compound | R2 | R3 | R5 | R6 | R7 | R15 | R18 | R19 | HIV protease inhibition rate (%) at 50 nM | Anti-HIV* IC50 (ng/ml) |
|---|---|---|---|---|---|---|---|---|---|---|
| Ex. 1 | OMe | H | Me | OH | H | Me | H | H | 95 | 17 |
| Ex. 2 | OMe | H | Me | OH | H | Me | F | H | 97 | 19 |
| Ex. 3 | OMe | H | Me | OH | F | Me | H | H | 93 | 13 |
| Ex. 4 | OMe | H | Cl | NH$_2$ | H | Me | H | H | 91 | 55 |
| Ex. 5 | OEt | H | Me | OH | H | Me | H | H | 95 | 6 |
| Ex. 6 | OCH$_2$ | O | Me | OH | H | Me | H | H | 97 | 32 |
| Ex. 7 | OnPr | H | Me | OH | H | Me | H | H | 97 | 16 |
| Ex. 8 | OiPr | H | Me | OH | H | Me | H | H | 96 | 11 |
| Ex. 9 | Me | H | Me | OH | H | Me | H | H | 97 | 20 |
| Ex. 10 | iPr | H | Me | OH | H | Me | H | H | 96 | 33 |
| Ex. 11 | Cl | H | Me | OH | H | Me | H | H | 97 | 23 |
| Ex. 12 | OEt | H | Cl | NH$_2$ | H | Me | H | H | 89 | 22 |
| Ex. 13 | OCH$_2$ | O | Cl | NH$_2$ | H | Me | H | H | 95 | 49 |
| Ex. 14 | OMe | H | Cl | NH$_2$ | H | Me | H | Me | 92 | 9 |
| Ex. 15 | OCH$_2$ | O | Cl | NH$_2$ | H | Me | H | Me | 96 | 13 |
| Re. 1 | H | H | Me | OH | H | Me | H | H | 96 | 49 |
| Re. 2 | H | H | Me | OH | H | Me | F | H | 98 | 22 |
| Re. 3 | H | H | Me | OH | F | Me | H | H | 88 | 55 |
| Re. 4 | H | H | Cl | NH$_2$ | H | Me | H | H | 91 | 98 |
| Re. 5 | nelfinavir | | | | | | | | 93 | 166 |

*In the presence of 50% human plasma.

Test Example 3

Measurement of protein binding rate

Preparation of samples (protein solution and drug solution)

Freezed human plasma (HFFPP100) was used after thawing. Powder of human alpha 1-acid glycoprotein (supplied by SIGMA Co., hereinafter abbreviated to AAG) was dissolved in a phosphate buffer solution (PBS, pH 7.0) to a concentration of 1 mg/ml. Drug solutions were prepared by dissolving the compounds synthesized in Example 1 and Reference Example 1 in dimethylsulfoxide in various concentrations.

Quantitative determination of unbound drug concentration

The drug solutions (10 µl, each) with different concentrations were added to 990 µl the plasma or AAG solutions prepared above, stirred well and incubated for 18 hours at 37° C. to equilibrate binding proteins. All amount of the solution was transferred to Micropartition Devices (Centrifree®, Millipore Co.) and filtered by centrifugation at 1500 ×g for 20 minutes (using TOMY CX-210 high-speed cooling centrifugal machine). 200 µl of the filtrate was directly subjected to HPLC (Type: HITACHI D-7000, column: COSMOSIL (4.6* 250 mm, manufactured by Nacalai Tesque Co., Ltd.). The HPLC analysis was carried out by using a 59:41 (v/v) water-acetonitrile mixture containing 0.1% trifluoroacetic acid (TFA) as a mobile phase and measuring absorbance at 210 nm. The quantitative determination of unbound drug concentration was carried out based on the absolute calibration curve method using a calibration line obtained from the analysis of a standard sample which contains the drug at a known concentration.

Analysis of protein binding properties

A commonly accepted method (see Y. Odagiri et al., Protein Binding Experimental Method (1991), Hirokawa Publishing Co., Ltd.) was employed for the analysis of protein binding properties.

In the analysis of the results of protein binding to human plasma, the ratio of unbound drug was determined by dividing the unbound drug concentration by the total drug concentration, and the unbound proportion was plotted against the logarithms of each drug concentration (FIG. 1). The plot was regressed with a straight line to compare the compounds of Reference Example 1 and Example 1. As a result, two regression formulas with a different inclination as shown in FIG. 1 were obtained, showing that the ratio of unbound drug on the compound of Example 1 was 0.029, twice or more the ratio on the compound of Reference Example 1 (0.013), when the concentration was 1 µM. Usefulness of the compound of Example 1 was thus confirmed.

The following method was used for the analysis of protein binding to AAG. The bound drug concentration (Cb) was determined by subtracting unbound drug concentration (Cu) from the total drug concentration. Then, the ratio Cb/Cu was plotted against Cb according to the following formula (2) to compare the inclination (-K) two compounds of the graph (Y. Odagiri et al., Protein Bond Experimental Method (1991), Hirokawa Publishing Co., Ltd.).

$$P+Cu \rightleftarrows Cb, \text{ therefore, } K=Cb/P*Cu \quad (1)$$

Insert P+Cb=n*Pt into the formula (1), $$Cb/Cu=-K*Cb+n*Pt*K \quad (2)$$

Figure 2:
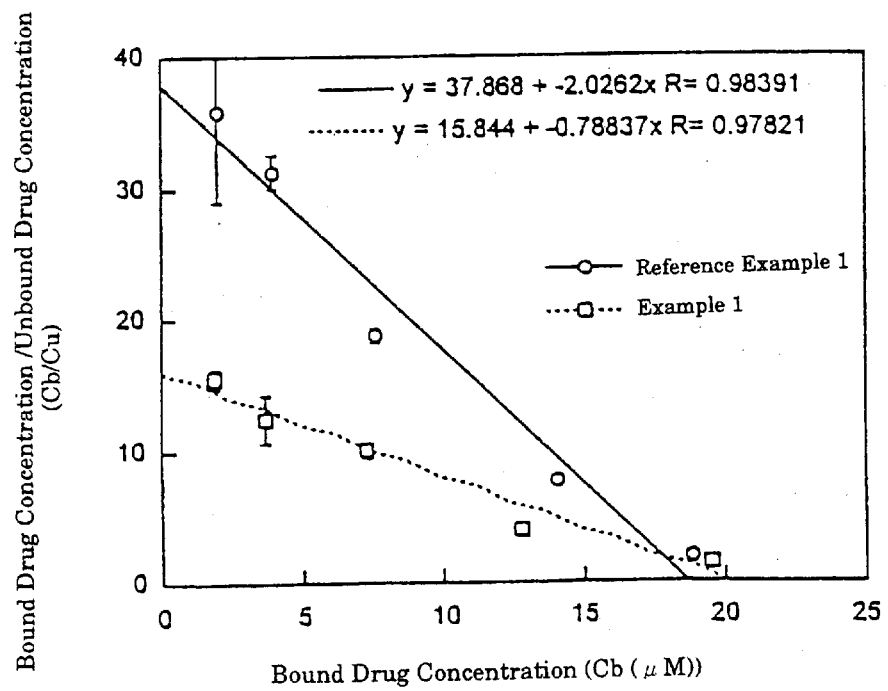
FIG. 2 shows the ratio of the bound drug concentration per unbound drug concentration (Cb/Cu) to AAG of the compounds of Example 1 and Reference Example 1, plotted against the bound drug concentration (Cb).

P: Concentration of all unbound sites of unbound protein
Cu: Unbound drug concentration
Cb: Bound drug concentration
Pt: Protein concentration
n: Number of drug molecules binding with molecular of protein
K: Binding constant The binding constant K to AAG of the compound of Reference Example 1 thus obtained was 2.03, whereas that of the compound of Example 1 was 0.78 (see FIG. 2). As clear from these data, the binding properties to AAG of the compound of Example 1 was shown to be weaker than the compound of Reference Example 1.

Test Example 4

A pharmacological experiment of the compound of the present invention was carried out using Sprague-Dawley rats (300–400 g). 10 mg/kg of a 50% polyethylene glycol (PEG) solution (1 ml/kg) was administered into the duodenum under anesthesia and blood was collected over time. After the addition of a solvent, the collected blood plasma sample was shaken and centrifuged. The organic layer was concentrated and dissolved in 50% methanol. The sample thus obtained was analyzed by HPLC for the determination of concentration of the compound in plasma. The HPLC analysis was carried out using Capecellpak C18 (4.6×150 mm, Shiseido LTD) as a column and a mixed solvent of 0.1% TFA aqueous solution and acetonitrile as an eluent (see T. Mimoto et al. J. Med. Chem., 42, 1789–1802, 1999).

The compound of the present invention was confirmed to have pharmacological characteristics expected as an in vivo effect of the compound. For instance, when the compound of Example 1 of the present invention is administered to a rat at a dose of 10 mg/kg into the duodenum, the compound is detected in plasma of the rat at a concentration of 0.42 µg/ml 30 minutes after the administration. This is significantly higher than the IC50 value (0.006 µg/ml) in an anti-virus test in the presence of 50% human blood serums.

Preparation Example 1

Standard dichotomy hard gelatin capsules were filled with 100 mg of the compound of Example 1 in the form of powder, 150 mg of lactose, 50 mg of cellulose, and 6 mg of magnesium stearate, each per capsule. The capsules were washed and dried.

Preparation Example 2

Tablets, each containing 100 mg of the compound of Example 1, 0.2 mg of colloidal silica, 5 mg of magnesium stearate, 275 mg of microcrystalline cellulose, 11 mg of starch, and 98.8 mg of lactose, were prepared according to a conventional method. The coating was applied to the tablets.

Industrial Applicability

The compound of the present invention exhibits superior anti-HIV activity, can maintain a high blood concentration in cells in the presence of plasma proteins, and exhibits strong activity. Therefore, the compound can decrease the effective concentration in clinical use.

What is claimed is:

1. A dipeptide compound represented by the following formula (I) or a pharmaceutically acceptable salt thereof,

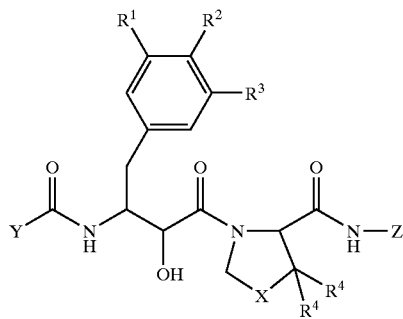

(I)

wherein $R^1$, $R^2$, and $R^3$ independently represent a linear or branched, saturated or unsaturated lower alkyl group, alkoxyl group, alkyl amino group, or dialkyl amino group having 1–4 carbon atoms (wherein a carbon atom is said alkyl, alkoxy, alkyl amino or dialkyl amino group is optionally replaced with an oxygen atom), a halogeno group, or a hydrogen atom, provided that all of the $R^1$, $R^2$, and $R^3$ are not a hydrogen atom at the same time, $R^2$ and $R^3$ may form a ring together;

$R^4$ represents a linear or branched lower alkyl group having 1–4 carbon atoms or a hydrogen atom;

X is methylene group or a sulfur atom;

Y represents a five or six member monocyclic or polycyclic hydrocarbon group, a heterocyclic group having a structure in which one or more carbon atom in the monocyclic or polycyclic hydrocarbon group is replaced by a heteroatom, an aryloxyalkyl group having 12 or less carbon atoms, in which the aromatic ring may be substituted with an alkyl group, alkoxy group, halogeno group, amino group or hydroxyl group; and Z represents art aliphatic hydrocarbon group having 1–6 carbon atoms or an aromatic hydrocarbon group having 12 or less carbon atoms in which the aromatic ring may be substituted with an alkyl group, alkoxy group, or halogeno group, or one or more carbon atom in the aromatic hydrocarbon group may be replaced by a heteroatom.

2. The dipeptide compound or pharmaceutically acceptable salt thereof according to claim 1, wherein Z is benzyl or substituted benzyl.

3. The dipeptide compound or pharmaceutically acceptable salt thereof according to claim 1, wherein Z is 1-indanyl or 2-indanyl.

4. A composition comprising a pharmaceutically acceptable carrier and a compound according to claim 1 in an amount effective to inhibit replication of human infectivity virus (HIV).

5. A dipeptide compound represented by the following formula (II) or a pharmaceutically acceptable salt thereof,

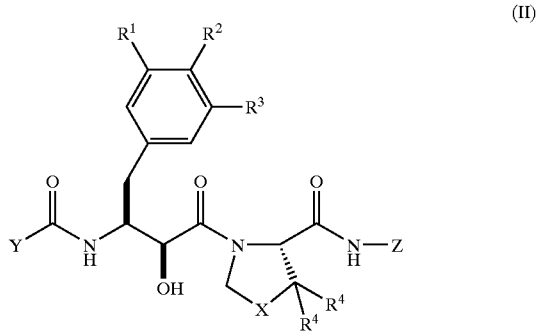

(II)

wherein $R^1$, $R^2$, and $R^3$ independently represent a linear or branched, saturated or unsaturated lower alkyl group, alkoxyl group, alkyl amino group, or dialkyl amino group having 1–4 carbon atoms (wherein a carbon atom in said alkyl, alkoxyl, alkyl amino or dialkyl amino group is optionally replaced with an oxygen atom), a halogeno group, or a hydrogen atom, provided that all of the $R^1$, $R^2$, and $R^3$ are not a hydrogen atom at the same time, $R^2$ and $R^3$ may form a ring together;

$R^4$ represents a linear or branched lower alkyl group having 1–4 carbon atoms or a hydrogen atom;

X is a methylene group or a sulfur atom;

Y represents a five or six member monocyclic or polycyclic hydrocarbon group, a heterocyclic group having a structure in which one or more carbon atoms in the monocyclic or polycyclic hydrocarbon group is replaced by a heteroatom, an aryloxyalkyl group having 12 or less carbon atoms, in which the aromatic ring may be substituted with an alkyl group, alkoxy group, halogeno group, amino group or hydroxyl group; and Z represents an aliphatic hydrocarbon group having 1–6 carbon atoms or an aromatic hydrocarbon group having 12 or less carbon atoms in which the aromatic ring may be substituted with an alkyl group, alkoxy group, or halogeno group, or one or more carbon atom in the aromatic hydrocarbon group may be replaced by a heteroatom.

6. A dipeptide compound represented by the following formula (I) or a pharmaceutically acceptable salt thereof, (I)

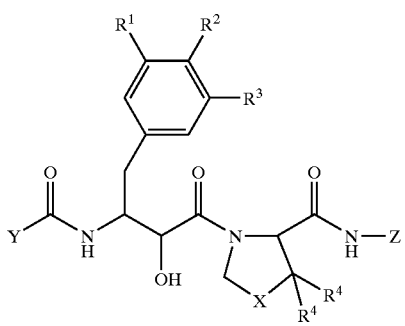

wherein $R^1$, $R^2$, and $R^3$ independently represent a linear or branched, saturated or unsaturated lower alkyl group, alkoxyl group, alkyl ammo group, or dialkyl amino group having 1–4 carbon atoms (wherein a carbon atom in said alkyl, alkoxyl, alkyl amino or dialkyl amino group is optionally replaced with an oxygen atom), a halogeno group, or a hydrogen atom, provided that all of the $R^1$, $R^2$, and $R^3$ are not a hydrogen atom at the same time, $R^2$ and $R^3$ may form a ring together;

$R^4$ represents a linear or branched lower alkyl group having 1–4 carbon atoms or a hydrogen atom;

X is a methylene group or a sulfur atom;

Y is a group represented by the following formula (III) or formula (IV); and Z is a group represented by the following formula (V) or formula (VI), or a linear or branched lower alkyl group having 6 or less carbon atoms;

(III)

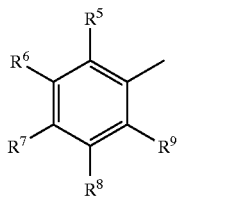

(IV)

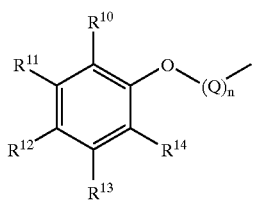

(V)

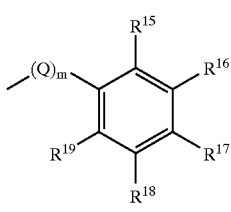

(VI)

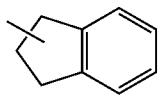

wherein $R^5$ represents a linear or branched lower alkyl group having 1–4 carbon atoms or a halogeno group, $R^6$ represents an amino group or hydroxyl group $R^7$, $R^8$, and $R^9$ respectively represent a hydrogen atom, methyl group, or fluoro group $R^{10}$, $R^{11}$, $R^{12}$, $R^{13}$ and $R^{14}$ individually represent a linear or branched lower alkyl or alkoxy group having 1–4 carbon atoms, halogeno group, or a hydrogen atom, $R^{15}$, $R^{16}$, $R^{17}$, $R^{18}$ and $R^{19}$ individually represent a linear or branched lower alkyl or alkoxy group having 1–4 carbon atoms, a halogeno group, or a hydrogen atom, and Q represents an alkylene group, n is 1, and m is 0–6.

7. A dipeptide compound represented by the following formula (II) or a pharmaceutically acceptable salt thereof, (II)

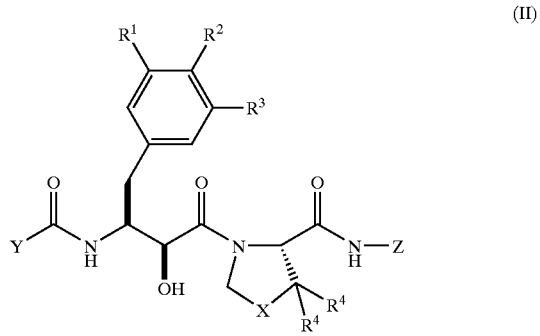

wherein $R^1$, $R^2$, and $R^3$ independently represent a linear or branched, saturated or unsaturated lower alkyl group, alkoxyl group, alkyl amino group, or dialkyl amino group having 1–4 carbon atoms (wherein a carbon atom in said alkyl, alkoxyl, alkyl amino or dialkyl amino group is optionally replaced with an oxygen atom), a halogeno group, or a hydrogen atom, provided that all of the $R^1$, $R^2$, and $R^3$ are not a hydrogen atom at the same time, $R^2$ and $R^3$ may form a ring together;

$R^4$ represents a linear or branched lower alkyl group having 1–4 carbon atoms or a hydrogen atom;

X is a methylene group or a sulfur atom;

Y is a group represented by be following formula (III) or formula (IV); and wherein Z is a group represented by the following formula (V), or formula (VI), or a linear or branched lower alkyl group having 6 or less carbon atoms;

(III)

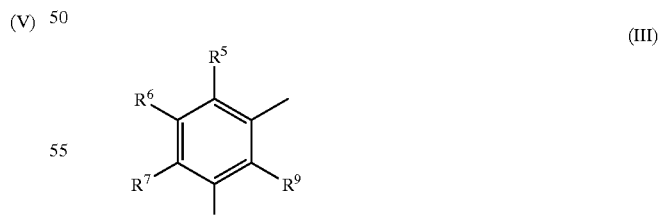

(IV)

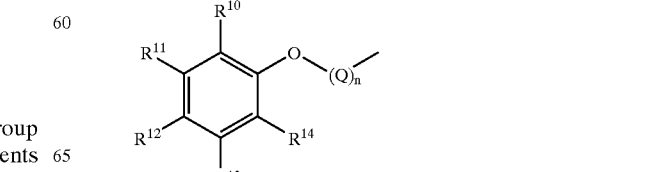

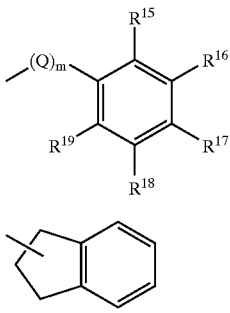

wherein R⁵ represents a linear or branched lower alkyl group having 1–4 carbon atoms or a halogeno group, R⁶ represents an amino group or hydroxyl group, R⁷, R⁸, and R⁹ respectively represent a hydrogen atom, methyl group, or fluoro group, R¹⁰, R¹¹, R¹², R¹³ and R¹⁴ individually represent a linear or branched lower alkyl or alkoxy group having 1–4 carbon atoms, a halogeno group, or a hydrogen atom, R¹⁵, R¹⁶, R¹⁷, R¹⁸ and R¹⁹ individually represent a linear or branched lower alkyl or alkoxy group having 1–4 carbon atoms, a halogeno group, or a hydrogen atom, and Q represents an alkylene group, n is 1, and m is 0–6.

8. The dipeptide compound or pharmaceutically acceptable salt thereof according to claim 6 or 7 wherein Z is benzyl or substituted benzyl.

9. The dipeptide compound or pharmaceutically acceptable salt thereof according to claim 6 or 7 wherein Z is 1-indanyl or 2-indanyl.

10. The dipeptide compound or pharmaceutically acceptable salt thereof according to claim 6 or claim 7 wherein R⁴ in formula (I) or (II) is a methyl group and X is sulfur.

11. The dipeptide compound or pharmaceutically acceptable salt thereof according to claim 10, wherein Y in formula (I) or (II) is the group represented by the formula (III) and Z is the group represented by the formula (V).

12. The dipeptide compound or pharmaceutically acceptable salt thereof according to claim 11, wherein R⁵ is a methyl group or chloro group, R⁶ is a hydroxyl group or amino group, and R⁷, R⁸, and R⁹ are a hydrogen atom.

13. The dipeptide compound or pharmaceutically acceptable salt thereof according to claim 12, wherein R¹⁵ is a methyl group, R¹⁶, R¹⁷ and R¹⁸ are a hydrogen atom, and R¹⁹ is a methyl group or a hydrogen atom.

14. The dipeptide compound or pharmaceutically acceptable salt thereof according to claim 13, wherein R¹ in the formula (I) or (II) is a hydrogen atom, and R² and R³ are respectively a linear or branched, saturated or unsaturated lower alkoxy group having 1–4 carbon atoms, in which the carbon atoms may be replaced by oxygen atoms, or a hydrogen atom (wherein R² and R³ are not simultaneously a hydrogen atom), or R² and R³ may form a ring in combination.

15. The dipeptide compound or pharmaceutically acceptable salt thereof according to claim 14, wherein R¹ in the formula (I) or (II) is a hydrogen atom, R² and R³ are respectively a methoxy group, or a hydrogen atom (wherein R² and R³ are not simultaneously a hydrogen atom), or R² and R³ may form a ring of methylenedioxy group in combination.

* * * * *